United States Patent [19]
Gonzalez et al.

[11] Patent Number: 5,856,454
[45] Date of Patent: Jan. 5, 1999

[54] CDNA FOR HUMAN AND PIG DIHYDROPYRIMIDINE DEHYDROGENASE

[75] Inventors: Frank J. Gonzalez; Pedro Fernandez-Salguero, both of Bethesda, Md.

[73] Assignee: The United States of America as represented by the Department of Health and Human Services, Washington, D.C.

[21] Appl. No.: 304,309

[22] Filed: Sep. 12, 1994

[51] Int. Cl.$^6$ .......................... C07H 21/02; C07H 21/04; C12Q 1/68

[52] U.S. Cl. .................... 536/23.1; 536/24.3; 536/24.31; 536/24.33; 435/6

[58] Field of Search .................................... 536/221, 231, 536/24.3, 24.31, 24.32, 24.33; 435/91.2, 6

[56] References Cited

FOREIGN PATENT DOCUMENTS

WO 92/13077  8/1992  WIPO .
WO 95/28489  10/1995  WIPO .

OTHER PUBLICATIONS

Boschman et al, "On–line sorting of human chromosomes by centromeric index and identification of sorted populations by GTG banding and fluorescent in situ hybridization", Hum. Genet. 85:41–48, 1990.

Sambrook et al, Molecular Cloning, A laboratory Manual, Cold Spring Harbor Laboratories, Cold Spring Harbor, New York, pp. 3.18 and 8.46–.8.49, 1989.

Genome systems packet, advertisement published in Biotechniques, vol. 17, No. 3 and attached sales information, Mar. 1994.

Lu, Zhi–Hong, et al. (1993) "Comparison of Dihydropyrimidine Dehydrogenase From Human, Rat, Pig and Cow Liver", *Biochemical Pharmacology*, 46(5):945–952.

Porter, David J. T., et al. (1991) "Inactivation of Dihydropyrimidine Dehydrogenase by 5–Iodouracil", *The Journal of Biological Chemistry*, 266(30):19988–19994.

Fujimoto, Shigeko, et al. (1991) "Effect of Vitamin B$_2$ Deficiency on Rat Liver Dihydropyrimidine Dehydrogenase Activity", *J. Nutri. Sci. Vitaminol.*, 37:89–98.

Shiotani, Taiichi, et al. (1981) "Purification and Properties of Dihydrothymine Dehydrogenase from Rat Liver", *The Journal of Biological Chemistry*, 256(1):219–224.

Lu, Zhi–Hong, et al. (1992) "Purification and Characterization of Dihydropyrimidine Dehydrogenase from Human Liver", *The Journal of Biological Chemistry*, 267(24): 17102–17109.

Houyau, Philippe, et al. (1993) "Severe Fluorouracil Toxicity in a Patient With Dihydropyrimidine Dehydrogenase Deficiency", *Journal of the National Cancer Institute*, vol. 85(19):1602–1603.

Tuchman, Mendel, et al. (1985) "Familial Pyrimidinemia and Pyrimidinuria Associated With Sever Fluorouracil Toxicity", *The New England Journal of Medicine*, 313:245–249.

Diasio, Robert B., et al. (1988) "Familial Deficiency of Dihydropyrimidine Dehydrogenase", *J. Clin. Invest.*, 81:47–51.

Podschun, Beate, et al. (1989) "Purification and characterization of dihydropyrimidine dehydrogenase from pig liver", *European Journal of Biochemistry* 185:219–224.

Bakkeren, J.A.J.M., et al. (1984) "Elevated urine, blood and cerebrospinal fluid levels of uracil and thymine in a child with dihydrothymine dehydrogenase deficiency", *Clinica Chimica Acta* 140:247–256.

Berger, R., et al. (1984) "Dihydropyrimidine dehydrogenase deficiency leading to thymine–uraciluria. An inborn error of pyrimidine metabolism", *Clinica Chimica Acta* 141: 227–234.

Lyss, Alan, P. et al. (1993) "Severe 5–Fluorouracil Toxicity in a Patient with Decreased Dihydropyrimidine Dehydrogenase Activity" *Cancer Investigation* 11(2):239–240.

Harris, Barry E., et al. (1991) "Severe 5–Fluorouracil Toxicity Secondary to Dihydropyrimidine Dehydrogenase Deficiency", *Cancer*, 68:499–501.

Piper, Anita A., et al. (1980) "The Activities of Thymidine Metabolishing Enzymes During The Cell Cycle of A Human Lymphocyte Cell Line LAZ–007 Synchronised by Centrifugal Elutriation", *Biochimica et Biophysica Acta*, 633:400–409.

Lu, Z–H, et al. (1994) "Genetic Polymorphism of Dihydropyrimidine Dehydrogenase (DPD): The Key Enzyme in 5–Fluorouracil", *Clinical Pharmacology & Therapeutics*, 55:180.

Cheng, X. et al. (1994) "Molecular Cloning of Dihydropyrimidine Dehydrogenase (DPD): Isolation of cDNA Fragments of Bovine Liver DPD", *Clinical Pharmacology & Therapeutics*, 55:188.

Podschun, B., et al., (1992) "Dihydropyrimidine Dehydrogenase: Isolation and Structural Analysis of the Native Enzyme and its Primary Proteolytic Fragments", *Journal of Biophysics*, 61 PT 2): A468.

(List continued on next page.)

*Primary Examiner*—Stephanie W. Zitomer
*Assistant Examiner*—Jeffrey Fredman
*Attorney, Agent, or Firm*—Townsend and Townsend and Crew LLP

[57] ABSTRACT

The invention relates to methods and compositions that are useful for detecting deficiencies in dihydropyrimidine dehydrogenase (DPD) levels in mammals including humans. Cancer patients having a DPD deficiency are at risk of a severe toxic reaction to the commonly used anticancer agent 5-fluorouracil (5-FU). Claimed are DPD genes from human and pig, methods for detecting the level of nucleic acids that encode DPD in a patient, and nucleic acids that are useful as probes for this purpose. Also claimed are methods for expressing DPD in heterologous organisms. Expression vectors that employ a DPD nucleic acid as a selectable marker are also claimed. This selectable marker functions in both prokaryotes and eukaryotes.

13 Claims, 9 Drawing Sheets

OTHER PUBLICATIONS

Fleming, R. et al. (1991) "Lethal toxicity and suspected dihydropyrimidine dehydrogenase deficiency in patients receiving 5-fluorouracil", *Proceedings of the American Association of Cancer Research*, 32:179.

Meinsma, R., et al. (1995) "Human Polymorphism in Drug Metabolism: Mutation in the Dihydropyrimidine Dehydrogenase Gene Results in Exon Skipping and Thymine Uracilurea", *DNA and Cell Biology*, 14(1):1–6.

Lu, Zhi–Hong, et al., (1992), "Purification and Characterization of Dihydropyrimidine Dehydrogenase from Human Liver", *The Journal of Biological Chemistry*, 267:24, pp. 17102–17106.

Lu, Zhihong, et al., (1993), "Dihydropyrimidine Dehydrogenase Activity in Human Peripheral Blood Mononuclear Cells and Liver: Population Characteristics, Newly Identified Deficient Patients, and Clinical Implication in 5–Fluorouracil Chemotherapy", *Cancer Research*, 53:5433–5438.

Figure 1A

HUMAN DIHYDROPYRIMIDINE DEHYDROGENASE cDNA SEQUENCE

```
   1 GCTGTCACTT GGCTCTCTGG CTGGAGCTTG AGGACGCAAG GAGGGTTTGT CACTGGCAGA
  61 CTCGAGACTG TAGGCACTGC CATGGCCCCT GTGCTCAGTA AGGACTCGGC GGACATCGAG
 121 AGTATCCTGG CTTTAAATCC TCGAACACAA ACTCATGCAA CTCTGTGTTC CACTTCGGCC
 181 AAGAAATTAG ACAAGAAACA TTGGAAAAGA AATCCTGATA AGAACTGCTT TAATTGTGAG
 241 AAGCTGGAGA ATAATTTTGA TGACATCAAG CACACGACTC TTGGTGAGCG AGGAGCTCTC
 301 CGAGAAGCAA TGAGATGCCT GAAATGTGCA GATGCCCCGT GTCAGAAGAG CTGTCCAACT
 361 AATCTTGATA TTAAATCATT CATCACAAGT ATTGCAAACA AGAACTATTA TGGAGCTGCT
 421 AAGATGATAT TTTCTGACAA CCCACTTGGT CTGACTTGTG AATCGTATG TCCAACCTCT
 481 GATCTATGTG TAGGTGGATG CAATTTATAT GCCACTGAAG AGGGACCCAT TAATATTGGT
 541 GGATTGCAGC AATTTGCTAC TGAGGTATTC AAAGCAATGA GTATCCCACA GATCAGAAAT
 601 CCTTCGCTGC CTCCCCAGA AAAAATGTCT GAAGCCTATT CTGCAAAGAT TGCTCTTTTT
 661 GGTGCTGGGC CTGCAAGTAT AAGTTGTGCT TCCTTTTTGG CTCGATTGGG GTACTCTGAC
 721 ATCACTATAT TTGAAAAACA AGAATATGTT GGTGGTTTAA GTACTTCTGA AATTCCTCAG
 781 TTCCGGCTGC CGTATGATGT AGTGAATTTT GAGATTGAGC TAATGAAGGA CCTTGGTGTA
 841 AAGATAATTT GCGGTAAAAG CCTTTCAGTG AATGAAATGA CTCTTAGCAC TTTGAAAGAA
 901 AAAGGCTACA AAGCTGCTTT CATTGGAATA GGTTTGCCAG AACCCAATAA AGATGCCATC
 961 TTCCAAGGCC TGACGCAGGA CCAGGGGTTT TATACATCCA AAGACTTTTT GCCACTTGTA
1021 GCCAAAGGCA GTAAAGCAGG AATGTGCGCC TGTCACTCTC CATTGCCATC GATACGGGGA
1081 GTCGTGATTG TACTTGGAGC TGGAGACACT GCCTTCGACT GTGCAACATC TGCTCTACGT
1141 TGTGGAGCTC GCCGAGTGTT CATCGTCTTC AGAAAAGGCT TTGTTAATAT AAGAGCTGTC
1201 CCTGAGGAGA TGGAGCTTGC TAAGGAAGAA AAGTGTGAAT TTCTGCCATT CCTGTCCCCA
1261 CGGAAGGTTA TAGTAAAAGG TGGGAGAATT GTTGCTATGC AGTTTGTTCG GACAGAGCAA
1321 GATGAAACTG GAAAATGGAA TGAAGATGAA GATCAGATGG TCCATCTGAA AGCCGATGTG
1381 GTCATCAGTG CCTTTGGTTC AGTTCGTGAGT GATCCTAAAG TAAAAGAAGC CTTGAGCCCT
1441 ATAAAATTTA ACAGATGGGG TCTCCCAGAA GTAGATCCAG AAACTATGCA AACTAGTGAA
1501 GCATGGGTAT TTGCAGGTGG TGATGTCGTT GGTTTGGCTA ACACTACAGT GGAATCGGTG
1561 AATGATGGAA AGCAAGCTTC TTGGTACATT CACAAATACG TACAGTCACA ATATGGAGCT
1621 TCCGTTTCTG CCAAGCCTGA ACTACCCCTC TTTTACACTC CTATTGATCT GGTGGACATT
1681 AGTGTAGAAA TGGCCGGATT GAAGTTTATA AATCCTTTTG GTCTTGCTAG CGCAACTCCA
1741 GCCACCAGCA CATCAATGAT TCGAAGAGCT TTTGAAGCTG GATGGGGTTT TGCCCTCACC
1801 AAAACTTTCT CTCTTGATAA GGACATTGTG ACAAATGTTT CCCCCAGAAT CATCCGGGGA
1861 ACCACCTCTG GCCCCATGTA TGGCCCTGGA CAAAGCTCCT TTCTGAATAT TGAGCTCATC
1921 AGTGAGAAAA CGGCTGCATA TTGGTGTCAA AGTGTCACTG AACTAAAGGC TGACTTCCCA
1981 GACAACATTG TGATTGCTAG CATTATGTGC AGTTACAATA AAAATGACTG GACGGAACTT
2041 GCCAAGAAGT CTGAGGATTC TGGAGCAGAT GCCCTGGAGT TAAATTTATC ATGTCCACAT
2101 GGCATGGGAG AAAGAGGAAT GGGCCTGGCC TGTGGGCAGG ATCCAGAGCT GGTGCGGAAC
2161 ATCTGCCGCT GGGTTAGGCA AGCTGTTCAG ATTCCTTTTT TTGCCAAGCT GACCCCAAAT
2221 GTCACTGATA TTGTGAGCAT CGCAAGAGCT GCAAAGGAAG GTGGTGCCAA TGGCGTTACA
2281 GCCACCAACA CTGTCTCAGG TCTGATGGGA TTAAAATCTG ATGGCACACC TTGGCCAGCA
2341 GTGGGGATTG CAAAGCGAAC TACATATGGA GGAGTGTCTG GACAGCAAT CAGACCTATT
2401 GCTTTGAGAG CTGTGACCTC CATTGCTCGT GCTCTGCCTG GATTTCCCAT TTTGGCTACT
2461 GGTGGAATTG ACTCTGCTGA AAGTGGTCTT CAGTTTCTCC ATAGTGGTGC TTCCGTCCTC
2521 CAGGTATGCA GTGCCATTCA GAATCAGGAT TTCACTGTGA TCGAAGACTA CTGCACTGGC
2581 CTCAAAGCCC TGCTTTATCT GAAAAGCATT GAAGAACTAC AAGACTGGGA TGGACAGAGT
2641 CCAGCTACTG TGAGTCACCA GAAAGGGAAA CCAGTTCCAC GTATAGCTGA ACTCATGGAC
2701 AAGAAACTGC AAGTTTTGG ACCTTATCTG AACAGCGCA AGAAAATCAT AGCAGAAAC
2761 AAGATTAGAC TGAAAGAACA AAATGTAGCT TTTTCACCAC TTAAGAGAAG CTGTTTTATC
2821 CCCAAAAGGC CTATTCCTAC CATCAAGGAT GTAATAGGAA AAGCACTGCA GTACCTTGGA
2881 ACATTTGGTG AATTGAGCAA CGTAGAGCAA GTTGTGGCTA TGATTGATGA AGAAATGTGT
2941 ATCAACTGTG GTAAATGCTA CATGACCTGT AATGATTCTG GCTACCAGGC TATACAGTTT
3001 GATCCAGAAA CCCACCTGCC CACCATAACC GACACTTGTA CAGGCTGTAC TCTGTGTCTC
3061 AGTGTTTGCC CTATTGTCGA CTGCATCAAA ATGGTTTCCA GGACAACACC TTATGAACCA
3121 AAGAGAGGCG TACCCTTATC TGTGAATCCG GTGTGTTAAG GTGATTTGTG AAACAGTTGC
3181 TGTGAACTTT CATGTCACCT ACATATGCTG ATCTCTTAAA ATCATGATCC TTGTGTTCAG
3241 CTCTTTCCAA ATTAAACAA ATATACATTT TCTAAATAAA AATATGTAAT TTCAAAATAC
3301 ATTTGTAAGT GTAAAAAATG TCTCATGTCA ATGACCATTC AATTAGTGGN CATAAAATAG
```

Figure 1B

```
3361 AATAATTCTT TTCTGAGGAT AGTAGTTAAA TAACTGTGTG GCAGTTAATT GGATGTTCAC
3421 TGCCAGTTGT CTTATGTGAA AAATTAACTT TTTGTGTGGC AATTAGTGTG ACAGTTTCCA
3481 AATTGCCCTA TGCTGTGCTC CATATTTGAT TTCTAATTGT AAGTGAAATT AAGCATTTTG
3541 AAACAAAGTA CTCTTTAACA TACAAGAAAA TGTATCCAAG GAAACATTTT ATCAATAAAA
3601 ATTACCTTTA ATTTAATGC TGTTTCTAAG AAAATGTAGT TAGCTCCATA AAGTACAAAT
3661 GAAGAAAGTC NAAAATTAT TTGCTATGGC AGGATAAGAA AGCCTAAAAT TGAGTTTGTN
3721 GGACTTTATT AAGTAAAATC CCCTTCGCTG AAATTGCTTA TTTTTGGTGT TGGATAGAGG
3781 ATAGGGAGAA TATTTACTAA CTAAATACCA TTCACTACTC ATGCGTGAGA TGGGTGTACA
3841 AACTCATCCT CTTTTAATGG CATTTCTCTT TAAACTATGT TCCTAACCAA ATGAGATGAT
3901 AGGATAGATC CTGGTTACCA CTCTTTTACT GTGCACATAT GGGCCCCGGA ATTC
```

Figure 2A

PIG DIHYDROPYRIMIDINE DEHYDROGENASE cDNA SEQUENCE

```
   1 TCGACCCACG CGTCCGCCGG CCGGAGGCGG AGGACGCGGG GAGGGCCCGC CGGTGGGAGA
  61 CTCCAAGCTG TCGGCATCGC CATGGCCCCT GTGCTGAGCA AGGACGTGGC GGACATCGAG
 121 AGTATCCTGG CTTTAAATCC TCGAACACAG TCTCATGCAG CCCTTCATTC CACTTTGGCC
 181 AAGAAATTGG ATAAGAAACA CTGGAAAAGA AATCCCGATA AGAACTGCTT TCATTGCGAG
 241 AAGCTGGAGA ATAATTTTGG TGACATCAAG CACACGACTC TTGGTGAGCG AGGAGCTCTC
 301 CGAGAAGCAA TGAGATGCCT GAAATGTGCC GATGCTCCCT GTCAGAAGAG CTGTCCAACT
 361 CATCTAGATA TCAAATCATT CATCACAAGT ATCTCAAATA AGAACTATTA TGGAGCTGCT
 421 AAGATGATTT TTTCTGACAA CCCTCTTGGT CTGACCTGTG AATGGTATG TCCAACCTCT
 481 GATCTTTGTG TAGGAGGATG CAATTTATAT GCAACTGAAG AGGGATCAAT TAATATTGGT
 541 GGATTGCAGC AGTTTGCTTC TGAGGTGTTC AAAGCAATGA ATATCCCACA AATCAGGAAT
 601 CCTTGTCTGC CATCCCAAGA GAAAATGCCT GAAGCTTATT CTGCAAAGAT TGCTCTTTTG
 661 GGTGCTGGGC CTGCAAGTAT AAGCTGTGCT TCCTTCTTGG CTCGATTAGG CTACTCTGAC
 721 ATCACTATAT TTGAAAAACA AGAATATGTT GGTGGTTTAA GTACTTCTGA AATCCCTCAG
 781 TTCCGGCTGC CATATGATGT AGTGAATTTT GAGATTGAGC TTATGAAGGA CCTTGGTGTA
 841 AAGATAATTT GTGGTAAAAG CCTTTCAGAG AATGAAATTA CTCTCAACAC TTTAAAAGAA
 901 GAAGGGTATA AAGCTGCTTT CATTGGTATA GGTTTGCCAG AACCCAAAAC GGATGACATC
 961 TTCCAAGGCC TGACACAGGA CCAGGGGTTT TACACATCCA AAGACTTTCT GCCCCTTGTA
1021 GCCAAAAGCA GTAAAGCAGG AATGTGTGCC TGTCACTCTC CATTGCCATC GATACGGGGA
1081 GCCGTGATTG TACTCGGAGC TGGAGACACA GCTTTCGACT GTGCAACATC CGCTTTACGT
1141 TGTGGAGCCC GCCGAGTGTT CCTCGTCTTC AGAAAAGGCT TTGTTAATAT AAGAGCTGTC
1201 CCTGAGGAGG TGGAGCTTGC TAAGGAAGAA AAATGTGAAT TTTTGCCTTT CCTGTCCCCA
1261 CGGAAGGTTA TAGTTAAAGG TGGGAGAATT GTTGCCGTGC AATTTGTTCG AACAGAACAA
1321 GATGAAACTG GAAAATGGAA TGAAGATGAA GATCAGATAG TCCATCTGAA GGCTGATGTG
1381 GTCATCAGTG CCTTTGGCTC AGTGCTGAGG GATCCTAAAG TAAAAGAAGC CTTGAGCCCT
1441 ATAAAATTTA ACAGATGGGA TCTCCCAGAA GTAGATCCAG AAACTATGCA AACCAGTGAA
1501 CCATGGGTGT TTGCAGGTGG TGATATCGTT GGTATGGCTA ACACTACGGT GGAATCCGTA
1561 AATGACGGAA AGCAGGCCTC CTGGTACATT CACAAATATA TCCAGGCCCA ATATGGAGCT
1621 TCAGTTTCTG CCAAGCCCGA ACTGCCCCTG TTTTATACGC CTGTTGACCT GGTGGACATC
1681 AGCGTGGAAA TGGCTGGATT AAAGTTTATA AATCCTTTTG GTCTTGCCAG TGCAGCTCCA
1741 ACTACCAGTT CATCGATGAT TCGAAGAGCT TTTGAAGCTG GATGGGGTTT TGCCCTGACC
1801 AAAACTTTCT CTCTTGATAA GGACATAGTG ACAAATGTCT CACCCAGAAT CGTCCGGGGG
1861 ACTACCTCTG GCCCCATGTA CGGCCCTGGA CAAAGCTCCT TCCTGAATAT TGAGCTCATC
1921 AGTGAAAAAA CAGCTGCATA TTGGTGTCAA AGTGTCACTG AACTAAAAGC TGACTTTCCA
1981 GACAATATTG TGATCGCCAG CATCATGTGT AGTTACAACA AAAATGACTG GATGGAACTC
2041 TCCAGAAAGG CTGAGGCCTC TGGAGCAGAT GCCTTGGAGT TAAATCTGTC ATGTCCACAC
2101 GGCATGGGAG AAAGAGGAAT GGGCCTGGCT TGTGGGCAGG ATCCAGAGCT GGTGCGGAAC
2161 ATCTGTCGCT GGGTTAGGCA AGCTGTTCAG ATTCCCTTTT TTGCCAAGTT GACCCCAAAC
2221 GTCACTGATA TAGTAAGCAT CGCCAGAGCG GCCAAGGAAG TGGCGCAGA TGGTGTTACA
2281 GCCACCAACA CGGTCTCAGG TCTCATGGGA TTAAAAGCCG ATGGCACGCC CTGGCCAGCG
2341 GTGGGTGCTG GCAAGCGGAC TACATACGGA GGAGTGTCTG GCACGGCCAT CAGACCAATT
2401 GCTTTGAGAG CTGTGACCAC CATTGCTCGT GCTTTGCCTG GATTTCCCAT TTTGGCTACT
2461 GGTGGAATTG ACTCAGCTGA AAGTGGACTT CAGTTTCTCC ACAGTGGTGC TTCGGTCCTC
2521 CAGGTATGCA GTGCTGTTCA GAATCAGGAT TTCACTGTCA TCCAAGACTA TTGCACTGGC
2581 CTCAAAGCCT TGCTTTATCT GAAAAGCATT GAAGAACTAC AAGGCTGGGA TGGGCAGAGT
2641 CCAGGTACCG AGAGTCACCA GAAGGGGAAA CCAGTTCCTC GTATTGCTGA ACTCATGGGA
2701 AAGAAACTGC CAAATTTTGG ACCTTATCTG GAGCAACGCA AGAAAATCAT AGCAGAGGAA
2761 AAGATGAGAC TGAAAGAACA AAATGCAGCT TTTCCACCAC TTGAGAGAAA ACCTTTTATT
2821 CCCAAAAAGC CTATTCCTGC TATTAAGGAT GTAATTGGAA AAGCACTGCA GTACCTTGGA
2881 ACGTTTGGTG AACTGAGCAA CATAGAGCAA GTTGTGGCTG TGATCGATGA AGAAATGTGT
2941 ATCAACTGTG GCAAATGCTA CATGACCTGT AATGACTCTG CTACCAGGC TATCCAGTTT
3001 GATCCCGAAA CCCACCTGCC CACCGTTACT GACACTTGCA CAGGCTGTAC CCTGTGTCTC
3061 TCCGTCTGCC CTATTATCGA CTGCATCAGA ATGGTTTCCA GGACAACACC TTACGAACCA
3121 AAGAGAGGCT TGCCCTTGGC TGTGAATCCG GTGTGCTGAG GTGATTCGTG AACAGTTGC
3181 TGTGAACTTT GAGGTCACCC CCATATGCTG TCTTTTTAAT TGTGGTTATT ATACTCATCT
3241 CTTTCTCAAT GAAAACAAAT ATAATATTTC TAGATAAAAG TTCTAAATAC ATGTCTAAAT
3301 TTTAAAAAAC ATCTACTGCC AGAGCCCGTT CAATTAATGG TCATAAAATA GAATCCTTCT
```

Figure 2B

```
3361 TTTCTGAGGC TAGTTGTTCA ATAACTGCTG CAGTTAATTG GATGTTCTCC ATCAGTTATC
3421 CATTATGAAA AATATTAACT TTTTTGGTGG CAATTTCCAA ATTGCCCTAT GCTGTGCTCT
3481 GTCTTTGATT TCTAATTGTA AGTGAAGTTA AGCATTTTAG AACAAAGTAT AATTTAACTT
3541 TCAAGCAAAT GTTTCCAAGG AAACATTTTA TAATTAAAAA TTACAATTTA ATTTTAACAC
3601 TGTTCCTAAG CAAATGTAAT TAGCTCCATA AAGCTCAAAT GAAGTCAAAT AATTATTTAC
3661 TGTGGCAGGA AAAGAAAGCC AATGAGGGTT TGCAAAACTT CTCTAAGGCC CTTTGGCTGA
3721 AATAACTTCT CTTTGGTGCT ACATACTGAA AGTGACTGTT TAATCATCAT TCATGTCACA
3781 CCGTGCTCCC TCGCCCTCAG GCCTGAGATG GGTCTCCAGA CTCCACCAGT GAATCAGCAT
3841 GACACCTTCT TTAACTGTGT GAGCGACGTT CCTAACAAAG TAAGGTGTGG GGATGAAGCT
3901 CTGGTTAAAG CCACTCTTTT GCTGTGCTCC GATCTGTTCT ATCCGCTTCT GAGAGCAACC
3961 TTCATGATTA CAGCAATTAA TGTTTGCACA GAGCCCAGAT TATACAGCAG TGGGTCATTG
4021 TGCTTCATTA TTCAAGAATG AAGATAAAGA CAAATAGAGG ATTAGTAAAA TATATTAAAT
4081 GTGCAATACC ACTTAAATGA CTCTTAATGT TTATATTGAA TTTCCAAAGC GATTAAATAA
4141 AAAAGAGCTA TTTTTTGTTA TTGCCAAACA ATATTTTTTG TATTTCTCTA TTTTCATAAT
4201 GAGCAAATAG CATCCTATAA ATCTGTTTAT CTCTTCTTTG TAGTGTGTTT TCATATAAAT
4261 CCACAAGTAG AAAATCTTTT CATCTGTGGC ATATTTCTAT GACAAATGCA AGATCTAGAA
4321 AAATTAAATG TTTGATTATG CCATTTTGGA AATGCATATT TACCACCAAA CCTATGTGAC
4381 TGAATAATGT CAAATAAAAT TTATGAATC ATTTTAAAAA AAAAAAAAAA AGGGCGGCCG
4441 C
```

Figure 3

```
MAPVLSKDVADIESILALNPRTQSHAALHSTLAKKLDKHWKRNPDKNCFHCEKLENNFGDIKHTTLGER      70
      S                T T C  S                N            D
GALREAMRCLKCADAPCQKSCPTHLDIKSFITSISNKNYYGAAKMIFSDNPLGLTCGMVCPTSDLCVGGC     140
                     N                 A
NLYATEEGSINIGGLQQFASEVFKAMNIPQIRNPCLPSQEKMPEAYSAKIALLGAGPASISCASFLARLG     210
            P        T        S       PP S                 F
YSDITIFEKQEYVGGLSTSEIPQFRLPYDVVNFEIELMKDLGVKIICGKSLSENEITLNTLKEEGYKAAF     280
                                                V   M S K
                                                    NADPH/NADP
IGIGLPEPKTDDIFQGLTQDQGFYTSKDFLPLVAKSSKAGMCACHSPLPSIRGA[VIVLGAGDTAFDCATS    350
     NK A                G
[ALRCGARRVFLVFRKGFVNIRAVPEEVELAKEEKCEFLPFLSPRKVIVKGGRIVAVQFVRTEQDETGKWN    420
       I                   M                          FAD
EDEDQIVHLKADVVISAFGSVERDPKVKEALSPIKFNRWDLPEVDPETMQ[TSEPWVFAGGD|VGMANTTV    490
                     S                          G    A        V L
ESVNDGKQASWYIHKYIQAQYGASVSAKPELPLFYTPVDLVDISVEMAGLKFINPFGLASAAPTTSSSMI    560
       V S                           I                           T A T
RRAFEAGWGFALTKTFSLDKDIVTNVSPRIVRGTTSGPMYGPGQSSFLNIELISEKTAAYWCQSVTELKA    630
                                I
DFPDNIVIASIMCSYNKNDWMELSRKAFEAS[GADALELNLSCPHGMGER]GMGLACGQDPELVRNICRWVRQ 700
          T          AK S D
                    URACIL
AVQIPFFAKLTPNVTDIVSIARAAKEGGADGVTATNIVSGLMGLKADGTPWPAVGAGKRTTYGGVSGTAI    770
                                         N                     IA
RPIALRAVTTIARALPGFPILATGGIDSAESGLQFLHSGASVLQVCSAVQNQDFTVIQDYCTGLKALLYL    840
                                                     I    E
KSIEELQGWDGQSPGTESHQKGKPVPRIAELMGKKLPNFGPYLEQRKKIIAEEKMRLKEQNAA[FPPLERK   910
        D         A V                        D S            N I  V S K S
PE[PKKPIPAIKDVIGKALQYLGTFGELSNIEQVVAVIDEEM[CINCGKCYMTCN]DSGYQAIQFDPETHLP  980
C  R            T                       V  M                 V SS
         [4Fe-4S]
TVTDT[CTGCTTCLCLSVCP]IDCIRMVSRTTPYEPKRGLPLAVNPVC*                         1025
I                    V  K
   [4Fe-4S]
```

CDNA FOR HUMAN AND PIG DIHYDROPYRIMIDINE DEHYDROGENASE

TECHNICAL FIELD OF THE INVENTION

The present invention relates to methods and compositions for detecting deficiencies in dihydropyrimidine dehydrogenase (DPD) levels in mammals, including humans. The methods and compositions are useful for identifying persons who are at risk of a toxic reaction to the commonly employed cancer chemotherapy agent 5-fluorouracil.

BACKGROUND OF THE INVENTION

5-Fluorouracil (5-FU) is commonly used in the treatment of cancers, including cancers of the breast, head, neck, and digestive system. The efficacy of 5-FU as a cancer treatment varies significantly among patients. Clinically significant differences in systemic clearance and systemic exposure of 5-FU are often observed. [Grem, J. L. In Chabner, B. A. and J. M. Collins (eds.), Cancer Chemotherapy: Principles and Practice, pp. 180–224, Philadelphia, Pa., Lippincott, 1990)]. Furthermore, 5-FU treatment is severely toxic to some patients, and has even caused death. [Fleming et al. (1993) Eur. J. Cancer 29A: 740–744; Thyss et al. (1986) Cancer Chemother. Pharmacol. 16: 64–66; Santini et al. (1989) Br. J. Cancer 59: 287-290; Goldberg et al. (1988) Br. J. Cancer 57: 186–189; Trump et al. (1991) J. Clin. Oncol. 9: 2027–2035; Au et al. (1982) Cancer Res. 42: 2930-2937].

Patients in whom 5-FU is severely toxic typically have low levels of dihydropyrimidine dehydrogenase (DPD) activity [Tuchman et al. (1985) N. Engl. J. Med. 313: 245–249; Diasio et al. (1988) J. Clin. Invest. 81: 47–51; Fleming et al. (1991) Proc. Am. Assoc. Cancer Res. 32: 179; Harris et al. (1991) Cancer (Phila.) 68: 499–501; Houyau et al. (1993) J. Nat'l. Cancer Inst. 85: 1602–1603; Lyss et al. (1993) Cancer invest. 11: 239–240]. Dihydropyrimidine dehydrogenase (DPD, EC 1.3.1.2) is the principal enzyme involved in the degradation of 5-FU, which acts by inhibiting thymidylate synthase [Heggie et al. (1987) Cancer Res. 47: 2203-2206; Chabner et al. (1989) In DeVita et al. (eds.), Cancer—Principles and Practice of Oncology, pp. 349–395, Philadelphia, Pa, Lippincott; Diasio et al. (1989) Clin. Pharmacokinet. 16: 215–237; Grem et al., supra.]. The level of DPD activity also affects the efficacy of 5-FU treatments, as 5-FU plasma levels are inversely correlated with the level of DPD activity [Iigo et al. (1988) Biochem. Pharm. 37: 1609–1613; Goldberg et al., supra.; Harris et al., supra.; Fleming et al., supra.]. In turn, the efficacy of 5-FU treatment of cancer is correlated with plasma levels of 5-FU.

In addition to its 5-FU degrading activity, DPD is also the initial and rate limiting enzyme in the three-step pathway of uracil and thymine catabolism, leading to the formation of β-alanine and β-aminobutyric acid, respectively [Wasternack et al. (1980) Pharm. Ther. 8: 629–665] DPD deficiency is associated with inherited disorders of pyrimidine metabolism, clinically termed thymine-uraciluria [Bakkeren et al. (1984) Clin. Chim. Acta. 140: 247–256]. Clinical symptoms of DPD deficiency include a nonspecific cerebral dysfunction, and DPD deficiency is associated with psychomotor retardation, convulsions, and epileptic conditions [Berger et al (1984) Clin. Chim. Acta 141: 227–234; Wadman et al. (1985) Adv. Exp. Med. Biol. 165A: 109–114; Wilcken et al. (1985) J. Inherit. Metab. Dis. 8 (Suppl. 2): 115–116; van Gennip et al. (1989) Adv. Exp. Med. Biol. 253A: 111–118; Brockstedt et al. (1990) J. Inherit. Metab. Dis. 12: 121–124; Duran et al. (1991) J. Inherit. Metab. Dis. 14: 367–370]. Biochemically, patients having DPD deficiency have an almost complete absence of DPD activity in fibroblasts [Bakkeren et al., supra.] and in lymphocytes [Berger et al., supra.; Piper et al. 1980) Biochim. Biophys. Acta 633: 400–409]. These patients typically have a large accumulation of uracil and thymine in their cerebrospinal fluid [Bakkeren et al., supra.] and urine [Berger et al., supra.; Bakkeren et al., supra.; Brockstedt et al., supra.; Fleming et al. (1992) Cancer Res. 52: 2899–2902].

Familial studies suggest that DPD deficiency follows an autosomal recessive pattern of inheritance [Diasio et al., (1988) supra.]. Up to three percent of the general human population are estimated to be putative heterozygotes for DPD deficiency, as determined by enzymatic activity in lymphocytes [Milano and Eteinne (1994) Pharmacogenetics (in press)]. This suggests that the frequency of homozygotes for DPD deficiency may be as high as one person per thousand.

DPD has been purified from liver tissue of rats [Shiotani and Weber (1981) J. Biol. Chem. 256: 219–224; Fujimoto et al. (1991); J. Nutr. Sci. Vitaminol. 37: 89–98], pig [Podschun et al. (1989) Eur. J. Biochem. 185: 219–224], cattle [Porter et al. (1991) J. Biol. Chem. 266: 9988–19994], and human [Lu et al. (1992) J. Biol. Chem. 267: 1702–1709]. The pig enzyme contains flavins and iron-sulfur prosthetic groups and exists as a homodimer with a monomer Mr of about 107,000 [Podschun et al., supra.]. Since the enzyme exhibits a nonclassical two-site ping-pong mechanism, it appears to have distinct binding sites for NADPH/NADP and uracil/5, 6-dihydrouracil [Podschun et al. (1990) J. Biol. Chem. 265: 12966–12972]. An acid-base catalytic mechanism has been proposed for DPD [Podschun et al. (1993) J. Biol. Chem. 268: 3407–3413].

Because an undetected DPD deficiency poses a significant danger to a cancer patient who is being treated with 5-FU, a great need exists for a simple and accurate test for DPD deficiency. Such a test will also facilitate diagnosis of disorders that are associated with DPD deficiency, such as uraciluria. The present invention provides such a test, thus fulfilling these and other needs.

SUMMARY OF THE INVENTION

The claimed invention includes isolated nucleic acids that code for a dihydropyrimidine dehydrogenase (DPD) protein. Human and pig DPD cDNA sequences are claimed (Seq. ID No. 1 and Seq. ID No. 3, respectively), as are DPD nucleic acids that are capable of selectively hybridizing to the human or pig DPD cDNAs under stringent hybridization conditions. Oligonucleotide probes that are capable of selectively hybridizing, under stringent hybridizing conditions, to a human or pig DPD nucleic acid are also claimed. The invention also includes isolated nucleic acids that code for a DPD polypeptide that specifically binds to an antibody generated against an immunogen consisting of a human or pig DPD polypeptide having an amino acid sequence as depicted by Seq. ID No. 2 or Seq. ID No. 4.

Also claimed are methods for determining whether a patient is at risk of a toxic reaction to 5-fluorouracil (5-FU). The methods involve analyzing DPD DNA or mRNA in a sample from the patient to determine the amount of intact DPD nucleic acid. An enhanced risk of a toxic reaction to 5-fluorouracil is indicated by a decrease in the amount of intact DPD DNA or mRNA in the sample compared to the amount of DPD DNA or mRNA in a sample obtained from a patient known to not have a DPD deficiency, or by a defect in the DPD nucleic acid that results in an inadequate level of DPD activity.

The invention also includes methods for expressing recombinant DPD protein in a prokaryotic cell. The methods involve transfecting the cell with an expression vector comprising a promoter that is operably linked to a nucleic acid that encodes DPD, and incubating the cell in a medium that contains uracil to allow expression of the recombinant DPD protein.

Also claimed are expression vectors that utilize a nucleic acid that encodes DPD as a selectable marker. These selectable markers function in both eukaryotes and prokaryotes.

BRIEF DESCRIPTION OF THE FIGURES

FIG. 1A-1., FIG. 1A-2, through FIG. 1B. show the nucleotide sequence of the human DPYD cDNA(SEQ ID No. 1)

FIGS. 2A-1., FIG. 2A-2., and FIG. 2B. shows the nucleotide sequence of the pig DPYD cDNA (SEQ ID No. 2).

FIG. 3-1. and FIG. 3-2, shows a comparison of the pig (SEQ ID No. 4) and human (SEQ ID No. 2) DPD cDNA deduced amino acid sequences. Only those amino acid residues of human DPD that differ from the pig sequences are shown below the pig DPD amino acid sequence. The following motifs relevant for catalytic activity are boxed: NADPH/NADP binding, FAD binding, uracil binding, and 4Fe-4S binding.

DESCRIPTION OF THE SPECIFIC EMBODIMENTS

Definitions

Figure 4:
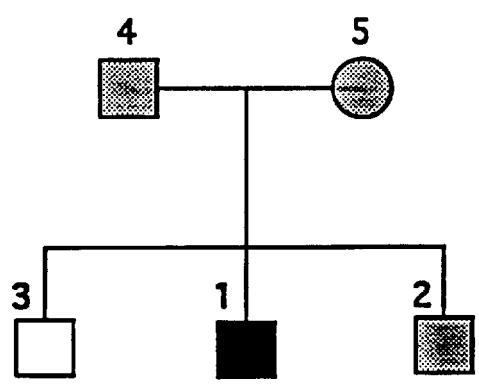
FIG. 4 shows the pedigree of a family used for a study of inheritance of DPD deficiency. Symbols are as follows: □ male, ○ female. Dotted symbols indicate intermediate DPD activity, a dashed square indicates high (normal) DPD activity, and ■ indicates undetectable DPD activity.

Abbreviations for the twenty naturally occurring amino acids follow conventional usage. In the polypeptide notation used herein, the left-hand direction is the amino terminal direction and the right-hand direction is the carboxy-terminal direction, in accordance with standard usage and convention.

The term "nucleic acids," as used herein, refers to either DNA or RNA. Included are single or double-stranded polymers of deoxyribonucleotide or ribonucleotide bases. Self-replicating plasmids, infectious polymers of DNA or RNA and nonfunctional DNA or RNA are included. Unless specified otherwise, the left hand end of single-stranded polynucleotide sequences is the 5' end. The direction of 5' to 3' addition of ribonucleotides to nascent RNA transcripts is referred to as the transcription direction; sequence regions on the DNA strand having the same sequence as the RNA and which are 5' to the 5' end of the RNA transcript are referred to as "upstream sequences;" sequence regions on the DNA strand having the same sequence as the RNA and which are 3' to the 3' end of the RNA transcript are referred to as "downstream sequences."

"Nucleic acid probes" or "oligonucleotide probes" can be DNA or RNA fragments. Where a specific sequence for a nucleic acid probe is given, it is understood that the complementary strand is also identified and included. The complementary strand will work equally well in situations where the target is a double-stranded nucleic acid.

The phrase "selectively hybridizing to" refers to a nucleic acid probe that, under appropriate hybridization conditions, hybridizes, duplexes or binds only to a particular target DNA or RNA sequence when the target sequences are present in a preparation of DNA or RNA. "Complementary" or "target" nucleic acid sequences refer to those nucleic acids that selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., *Molecular Cloning*: A Laboratory Manual (2nd ed.), Vols. 1–3, Cold Spring Harbor Laboratory, (1989) or Current Protocols in Molecular Biology, F. Ausubel et al., (ed.) Greene Publishing and Wiley-lnterscience, New York (1987).

The terms "stringent conditions" and "conditions of high stringency" refer to conditions under which a nucleic acid probe will hybridize substantially to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a complementary probe. Typically, stringent conditions will be those in which the salt concentration is at least about 0.2 molar at pH 7 and the temperature is at least about 60° C. for long sequences (e.g. greater than about 50 nucleotides) and at least about 42° C. for shorter sequences (e.g. 10 to 50 nucleotides). As other factors may significantly affect the stringency of hybridization, including, among others, base composition and size of the complementary strands, the presence of organic solvents and the extent of base mismatching, the combination of parameters is more important than the absolute measure of any one.

A nucleic acid is said to "encode" or "code for" a specific protein when the nucleic acid sequence comprises, in the proper order, codons for each of the amino acids of the protein or a specific subsequence of the protein. The nucleic acids include both the DNA strand that is transcribed into RNA and the RNA strand that is translated into protein. It is further understood that the invention includes nucleic acids that differ from the DPD sequences specifically disclosed herein in that particular codons are replaced by degenerate codons, so that the variant nucleic acid encodes a protein having the same amino acid sequence as that encoded by the specifically disclosed nucleic acids.

The phrase "isolated" or "substantially pure," when referring to nucleic acids that encode DPD, refers to nucleic acids that are sufficiently pure that the predominant nucleic acid species in the preparation is the desired DPD nucleic acid. Preferably, the DPD nucleic acids are more than 70% pure, more preferably greater than 90% pure, and most preferably greater than 95% pure.

The term "control sequence" refers to a DNA sequence or sequences that are capable, when properly attached to a desired coding sequence, of causing expression of the coding sequence. Such control sequences include at least promoters and, optionally, transcription termination signals. Additional factors necessary or helpful for expression can also be included. As used herein, "control sequences" simply refers to whatever DNA sequence signal that is useful to result in expression in the particular host used. Often, control sequences are utilized as an "expression cassette," in which the control sequences are operably linked to the nucleic acid that is to be expressed.

The term "operably linked" as used herein refers to a juxtaposition wherein the components are configured so as to perform their usual function. Thus, control sequences or promoters operably linked to a coding sequence are capable of effecting the expression of the coding sequence.

The term "vector" refers to nucleic acids that are capable of replicating in a selected host organism. The vector can replicate as an autonomous structure, or alternatively can integrate into the host cell chromosome(s) and thus replicate along with the host cell genome. Vectors include viral- or bacteriophage-based expression systems, autonomous self-replicating circular DNA (plasmids), and include both expression and nonexpression vectors. The term "plasmid" refers to an autonomous circular DNA molecule capable of replication in a cell, and includes both the expression and nonexpression types.

The phrase "recombinant protein" or "recombinantly produced protein" refers to a peptide or protein produced using recombinant DNA techniques. Host cells produce the recombinant protein because they have been genetically altered by the introduction of the appropriate nucleic acid that codes for the protein. Typically, the heterologous nucleic acid is introduced as part of an expression vector.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence can comprise a complete cDNA or gene sequence, such as the nucleic acid sequence of Seq. ID Nos. 1 or 3, or can be a subset of a larger sequence, for example, as a segment of a full-length cDNA or gene sequence.

Optimal alignment of sequences for aligning a comparison window can be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci. (USA)* 85:2444, or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.).

The terms "substantial identity" or "substantial sequence identity" as applied to nucleic acids and as used herein denote a characteristic of a nucleotide sequence wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25–50 nucleotides. The percentage of sequence identity is calculated by comparing the reference sequence to the polynucleotide sequence, which may include deletions or additions which total 20 percent or less of the reference sequence over the window of comparison. The reference sequence may be a subset of a larger sequence, such as a segment or subsequence of the human DPD gene disclosed herein.

As applied to polypeptides, the terms "substantial identity" or "substantial sequence identity" mean that two peptide sequences, when optimally aligned, such as by the programs GAP or BESTFIT using default gap weights, share at least 80 percent sequence identity, preferably at least 90 percent sequence identity, more preferably at least 95 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions that are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a DPD polypeptide means a chemical composition that is essentially free of other cellular components. The DPD polypeptide is preferably in a homogeneous state, although it can be in either a dry form or in an aqueous solution. Purity and homogeneity are typically determined using analytical chemistry techniques such as polyacrylamide gel electrophoresis (PAGE) or high performance liquid chromatography (HPLC). A protein that is the predominant species present in a preparation is considered substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with," when referring to a protein or peptide, refers to a binding reaction that is determinative of the presence of the protein in the presence of a heterogeneous population of proteins and other biologics. Thus, under designated immunoassay conditions, the specified antibodies bind to a particular protein and do not bind in a significant amount to other proteins present in the sample. Obtaining an antibody that specifically binds to a particular protein may require screening. For example, antibodies raised to the human DPD protein immunogen with the amino acid sequence depicted in SEQ. ID No. 2 can be selected to obtain antibodies specifically immunoreactive with DPD proteins and not with other proteins. These antibodies recognize proteins that are homologous to the human DPD protein, such as DPD proteins from other mammalian species. A variety of immunoassay formats can be used to select antibodies specifically immunoreactive with a particular protein. For example, solid-phase enzyme-linked immunoassays (ELISAs) are routinely used to select monoclonal antibodies specifically immunoreactive with a protein. See Harlow and Lane (988) *Antibodies*, A Laboratory Manual, Cold Spring Harbor Publications, New York, for a description of immunoassay formats and conditions that can be used to determine specific immunoreactivity.

Detailed Description of the Preferred Embodiment

The claimed invention provides compositions and methods that are useful for detecting deficient or diminished DPD activity in mammals, including humans. These methods and compositions are useful for identifying people who are at risk of a toxic reaction to the chemotherapy agent 5-fluorouracil. Methods and compositions for treating mammals who suffer from an insufficient level of DPD are also provided. Also included in the invention are methods for expressing high levels of DPD in prokaryotes, and selectable markers that function in both prokaryotes and eukaryotes.

The claimed methods and compositions are based on the discovery of an isolated cDNA that codes for human dihydropyrimidine dehydrogenase (DPD). A newly discovered cDNA that codes for pig DPD is also described. The human (SEQ. ID No. 1) and pig (SEQ. ID No. 3) DPD cDNA sequences are presented in FIG. 1A-1., FIG. 1A-2. through FIG.1B., FIG. 2A-1., FIG. 2A-2., and FIG. 2B. respectively. An alignment of the human and pig DPD deduced amino acid sequences is shown in FIG. 3. The nucleic acids of the invention are useful for determining whether a patient has an abnormal DPD gene, or whether the DPD gene in a patient is expressed an insufficient level. Either of these conditions can result in a DPD deficiency that can cause the patient to be susceptible to 5-FU toxicity. By detecting the DPD deficiency before treatment commences, the clinician can either adjust the dose of 5-FU downward, or can choose an alternative chemotherapy agent.

A. Description and Isolation of DPD Nucleic Acids

1. Description of DPD Nucleic Acids

The nucleic acids of the invention are typically identical to or show substantial sequence identity (determined as described above) to the nucleic acid sequences of SEQ ID No. 1 or SEQ ID No. 3. Nucleic acids encoding human DPD will typically hybridize to the nucleic acid sequence of SEQ ID Nos. 1 or 3 under stringent hybridization conditions as described herein.

Also claimed are isolated nucleic acids that code for a DPD polypeptide that specifically binds to an antibody generated against a specific immunogen, such as an immunogen that has of the amino acid sequence depicted by SEQ ID Nos. 2 or 4, or a specific subsequence of these polypeptides. To identify whether a nucleic acid encodes such a DPD polypeptide, an immunoassay is typically employed. Typically, the immunoassay will use a polyclonal or monoclonal antibody that was raised against the protein of SEQ ID Nos. 2 or 4. The antibody is selected to have low cross-reactivity against other (non-DPD) polypeptides, and any such cross- reactivity is removed by immunoadsorption prior to use in the immunoassay.

In order to produce antisera for use in an immunoassay, the DPD protein of SEQ ID Nos. 2 or 4 is isolated as described herein, for example, by recombinant expression. An inbred strain of mouse such as Balb/c is immunized with the DPD protein using a standard adjuvant, such as Freund's adjuvant, and a standard mouse immunization protocol (see Harlow and Lane, supra). Alternatively, a synthetic peptide derived from the amino acid sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against non-DPD proteins, using a competitive binding immunoassay such as the one described in Harlow and Lane, supra, at pages 570–573. Three non-DPD proteins are used in this determination: the IRK protein [Kubo et al. (1993) *Nature* 362:127], the G-IRK protein [Kubo et al. (1993) *Nature* 364:802] and the ROM-K protein [Ho et al. (1993) *Nature* 362:127]. These non-DPD proteins can be produced as recombinant proteins and isolated using standard molecular biology and protein chemistry techniques as described herein.

Immunoassays in the competitive binding format can be used for the crossreactivity determinations. For example, the DPD protein of SEQ ID Nos. 2 or 4 can be immobilized to a solid support. Proteins added to the assay compete with the binding of the antisera to the immobilized antigen. The ability of the above proteins to compete with the binding of the antisera against the immobilized protein is compared to the DPD protein of Seq. ID Nos. 2 or 4. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoadsorption with the above-listed proteins.

The immunoadsorbed and pooled antisera are then used in a competitive binding immunoassay as described above to determine whether a nucleic acid codes for a DPD polypeptide that specifically binds to an antibody generated against human or pig DPD polypeptide of SEQ ID No. 2 or 4, respectively. The second protein (the protein encoded by the nucleic acid of interest) and the immunogen protein (the human or pig DPD protein of SEQ ID Nos. 2 or 4) are compared for their ability to inhibit binding of the antiserum to immobilized human or pig DPD polypeptide. In order to make this comparison, the two proteins are each assayed at a wide range of concentrations to determine the amount of each protein required to inhibit the binding of the antisera to the immobilized protein by 50%. If the amount of the second protein required is less than 10 times the amount of the human DPD protein of SEQ ID No. 2 that is required, then the second protein is said to specifically bind to an antibody generated to an immunogen consisting of the human DPD protein of SEQ ID No. 2. Similarly, the second protein is said to specifically bind to an antibody generated against an immunogen consisting of the pig DPD protein of SEQ ID No. 4 if the amount of second protein required to block antiserum binding by 50% is ten times or less than the amount of pig DPD protein required.

2. Isolation of DPD Nucleic Acids

The DPD nucleic acid compositions of this invention, whether cDNA, genomic DNA, RNA, or a hybrid of the various combinations, may be isolated from natural sources or may be synthesized in vitro. The nucleic acids claimed can be present in transformed or transfected whole cells, in a transformed or transfected cell lysate, or in a partially purified or substantially pure form.

Techniques for manipulating the DPD and other nucleic acids, such as those techniques used for subcloning the nucleic acids into expression vectors, labelling probes, nucleic acid hybridization, and the like are described generally in Sambrook et al., *Molecular Cloning—A Laboratory Manual* (2nd Ed.), Vol. 1–3, Cold Spring Harbor Laboratory, Cold Spring Harbor, N.Y., 1989, which is incorporated herein by reference. This manual is hereinafter referred to as "Sambrook."

Various methods for isolating the DPD nucleic acids are available. For example, one can isolate DNA from a genomic or cDNA library by using labelled oligonucleotide probes that have nucleotide sequences that are complementary to the human and pig DPD gene sequences disclosed herein (SEQ. ID Nos. 1 and 3, respectively). One can use full-length probes or oligonucleotide probes that are based on specific subsequences of these genes. Probes are discussed more fully below. One can use such probes directly in hybridization assays to identify nucleic acids that code for DPD, or one can use amplification methods such as PCR to isolate DPD nucleic acids.

Methods for making and screening cDNA libraries are well known. See, e.g., Gubler, U. and Hoffman, B. J. (1983) Gene 25: 263–269 and Sambrook, supra. Briefly, to prepare a cDNA library for the purpose of isolating a DPD cDNA, one isolates mRNA from tissue that expresses DPD. Liver is a particularly useful tissue for this purpose, as are peripheral blood lymphocytes. Most other cells also likely produce DPD due to its critical role in pyrimidine degradation and β-alanine synthesis. cDNA is then prepared from the mRNA using standard techniques and ligated into a recombinant vector. The vector is transfected into a recombinant host for propagation, screening and cloning.

Methods for preparing genomic libraries are also well known to those of skill in the art. See, e.g., Sambrook, supra. Typically, one can prepare a genomic library by extracting DNA from tissue and either mechanically shearing or enzymatically digesting the DNA to yield fragments of about 12–20 kb, or longer if a cosmid is used as the cloning vector. Fragments of the desired size are purified by density gradient centrifugation or gel electrophoresis. The fragments are then cloned into suitable cloning vectors, such as bacteriophage lambda vectors or cosmids. If phage or cosmids are used, one then packages the DNA in vitro, as described in Sambrook, supra. Recombinant phage or cosmids are analyzed by plaque hybridization as described in Benton and Davis, (1977) *Science* 196: 180–182. Colony hybridization is carried out as generally described in Grunstein et al. (1975) *Proc. Natl. Acad. Sci. USA.* 72: 3961–3965.

Standard techniques are used to screen the cDNA or genomic DNA libraries to identify those vectors that contain a nucleic acid that encodes a human or mammalian DPD. For example, Southern blots are utilized to identify those library members that hybridize to nucleic acid probes derived from the human or pig DPD nucleotide sequences shown in FIG. 1A-1. FIG. 1A-2. through FIG. 1B., FIG.2A-1., FIG. 2A-2., and FIG. 2B., respectively. See, e.g., Sambrook, supra.

Alternatively, one can prepare DPD nucleic acids by using any of various methods of amplifying target sequences, such as the polymerase chain reaction. For example, one can use polymerase chain reaction (PCR) to amplify DPD nucleic acid sequences directly from mRNA, from cDNA or genomic DNA, or from genomic DNA libraries or cDNA libraries. Briefly, to use PCR to isolate the DPD nucleic acids from genomic DNA, one synthesizes oligonucleotide primer pairs that are complementary to the 3' sequences that flank the DNA region to be amplified. One can select primers to amplify the entire region that codes for a full-length DPD polypeptide, or to amplify smaller DNA segments that code for part of the DPD polypeptide, as desired. Suitable primer pairs for amplification of the human DPYD gene are shown in Table 1 and are listed as SEQ ID Nos. 5 and 6, 7 and 8, 9 and 10. Polymerase chain reaction is then carried out using the two primers. See, e.g., *PCR Protocols: A Guide to Methods and Applications.* (Innis, M, Gelfand, D., Sninsky, J. and White, T., eds.), Academic Press, San Diego (1990). Amplified fragments can be used as hybridization probes to identify other DPD nucleic acids, such as those from organisms other than human and pig.

Other methods known to those of skill in the art can also be used to isolate DNA encoding the DPD polypeptides. See, e.g., Sambrook, supra., for a description of other techniques that are useful for isolating DNA that codes for specific polypeptides.

B. Diagnostic Methods: Detection of DPD Deficiency by Nucleic Acid Detection

To permit the clinician to determine whether a patient has diminished or deficient DPD activity, and thus an enhanced risk of a toxic reaction to 5-FU, the present invention provides methods and reagents for detecting DNA and RNA molecules that code for DPD. These methods permit one to detect DPD deficiency in a patient whether the deficiency is due to a deleted DPD gene (DPYD), a DPD gene that is expressed at a lower than normal rate, or a missense or nonsense mutation that results in an abnormal DPD polypeptide. If any of these tests indicate that the patient has a DPD deficiency, the clinician should exercise extreme caution in using 5-FU as a chemotherapy agent. These methods are also suitable for diagnosing other disorders that are caused by DPD nucleic acid deficiency, such as thymine uraciluria.

1. Oligonucleotide Probes

One aspect of the invention is nucleic acid probes that are useful for detecting the presence or absence of DPD nucleic acids in a sample from a human or other mammal. Typically, oligonucleotides are used, although longer fragments that comprise most or all of a DPD gene are also suitable. The claimed probes are specific for human or pig DPD genes. Oligonucleotide probes are generally between about 10 and 100 nucleotides in length, and are capable of selectively hybridizing, under stringent hybridizing conditions, to a target region, a specific subsequence of a DPD nucleic acid. The probes selectively hybridize to DPD nucleic acids, meaning that under stringent hybridization conditions the probes do not substantially hybridize to non-DPD nucleic acids (less than 50% of the probe molecules hybridize to non-DPD nucleic acids). One of skill will recognize that oligonucleotide probes complementary to specific subsequences of the target regions, but not to the entire target region, will also function in the claimed assays so long as such probes selectively hybridize to the target regions.

Alternatively, the oligonucleotide probe can comprise a concatemer that has the formula [X-Y-Z]n, wherein:
 a) X is a sequence of 0 to 100 nucleotides or nucleotide analogs that are not complementary to a DPD nucleic acid;
 b) Y is a sequence of 10 to 100 nucleotides or nucleotide analogs that are capable of hybridizing under stringent hybridizing conditions to a DPD nucleic acid;
 c) Z is a sequence of nucleotides the same as or different from X, such that nucleotides or nucleotide analogs are not complementary to a DPD nucleic acid; and
 d) n is 1–500, or more and, where n is greater than 1, Y can be the same or different sequences of nucleotides having the indicated hybridization capability. The probe can be free or contained within a vector sequence (e.g., plasmids or single stranded DNA).

The degree of complementarity (homology) required for detectable binding with the DPD nucleic acids will vary in accordance with the stringency of the hybridization medium and/or wash medium. The degree of complementarity will optimally be 100 percent; however, it should be understood that minor variations in the DPD nucleic acids may be compensated for by reducing the stringency of the hybridization and/or wash medium as described below. Thus, despite the lack of 100 percent complementarity under reduced conditions of stringency, functional probes having minor base differences from their DPD nucleic acid targets are possible. Therefore, under hybridization conditions of reduced stringency, it may be possible to modify up to 60% of a given oligonucleotide probe while maintaining an acceptable degree of specificity. In addition, analogs of nucleosides may be substituted within the probe for naturally occurring nucleosides. This invention is intended to embrace these species when referring to polynucleic acid probes.

Suitable oligonucleotide probes include synthetic oligonucleotides, cloned DNA fragments, PCR products, and RNA molecules. The nature of the probe is not important, provided that it hybrid and not to other nucleic acids, and not to other nucleic acids under stringent hybridization conditions.

To obtain large quantities of DNA or RNA probes, one can either clone the desired sequence using traditional cloning methods, such as described in Sambrook et al., *Molecular Cloning. A Laboratory Manual*, Cold Spring Harbor, N.Y., 1989, or one can produce the probes by chemical synthesis using commercially available DNA synthesizers. An example of cloning would involve insertion of all or part of the cDNA for the human or pig DPD gene into a replication vector, such as pBR322, M13, or into a vector containing the SP6 promotor (e.g., for generation of single-stranded DPD RNA using SP6 RNA polymerase), and transformation of a bacterial host. The probes can be purified from the host cell by lysis and nucleic acid extraction, treatment with selected restriction enzymes, and further isolation by gel electrophoresis.

Oligonucleotide probes can be chemically synthesized using commercially available methods and equipment. For example, the solid phase phosphoramidite triester method first described by Beaucage and Carruthers [(1981) *Tetrahedron Lett.* 22: 1859–1862] is suitable. This method can be used to produce relatively short probes of between 10 and 50 bases. The triester method described by Matteucci et al. [(1981) *J. Am. Chem. Soc.,* 103:3185] is also suitable for synthesizing oligonucleotide probes. Conveniently, one can use an automated oligonucleotide synthesizer such as the Model 394 DNA/RNA Synthesizer from Applied Biosystems (Foster City, Calif.) using reagents supplied by the same company.

After synthesis, the oligonucleotides are purified either by native acrylamide gel electrophoresis or by anion-exchange HPLC as described in, for example, Pearson and Regnier (1983) *J. Chrom.* 255: 137–149. The sequence of the synthetic oligonucleotide can be verified using the chemical degradation method of Maxam, A. M. and Gilbert, W. (1980) In Grossman, L. and Moldave, D., eds. Academic Press, New York, *Methods in Enzymology,* 65:499–560.

Probes can be comprised of the natural nucleotides or known analogs of the natural nucleotides, including those modified to bind labeling moieties. Oligonucleotide probes that comprise thionucleotides, and thus are resistant to nuclease cleavage, are also suitable. One can use probes that are the full length of the DPD coding regions, or probes that hybridize to a specific subsequence of a DPD gene. Shorter probes are empirically tested for specificity. Preferably, nucleic acid probes are 15 nucleotides or longer in length, although oligonucleotide probe lengths of between about 10 and 100 nucleotides or longer are appropriate. Sambrook, supra describes methods for selecting nucleic acid probe sequences for use in nucleic acid hybridization.

For purposes of this invention, the probes are typically labelled so that one can detect whether the probe has bound to a DPD nucleic acid. Probes can be labeled by any one of several methods typically used to detect the presence of hybrid polynucleotides. The most common method of detection is the use of autoradiography using probes labeled with $^3$H, $^{125}$I, $^{35}$S, $^{14}$C, $^{32}$P, or the like. The choice of radioactive isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The choice of label dictates the manner in which the label is bound to the probe. Radioactive probes are typically made using commercially available nucleotides containing the desired radioactive isotope. The radioactive nucleotides can be incorporated into probes, for example, by using DNA synthesizers, by nick translation or primer extension with DNA polymerase I, by tailing radioactive nucleotides to the 3' end of probes with terminal deoxynucleotidyl transferase, by incubating single-stranded M13 plasmids having specific inserts with the Klenow fragment of DNA polymerase in the presence of radioactive deoxynucleotides, dNTP, by transcribing from RNA templates using reverse transcriptase in the presence of radioactive deoxynucleotides, dNTP, or by transcribing RNA from vectors containing specific RNA viral promoters (e.g., SP6 promoter) using the corresponding RNA polymerase (e.g., SP6 RNA polymerase) in the presence of radioactive ribonucleotides rNTP.

The probes can be labeled using radioactive nucleotides in which the isotope resides as a part of the nucleotide molecule, or in which the radioactive component is attached to the nucleotide via a terminal hydroxyl group that has been esterified to a radioactive component such as inorganic acids, e.g., $^{32}$P phosphate or $^{14}$C organic acids, or esterified to provide a linking group to the label. Base analogs having nucleophilic linking groups, such as primary amino groups, can also be linked to a label.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, as described in Renz. M., and Kurz, K. (1984) A Colorimetric Method for DNA Hybridization. *Nucl. Acids Res.* 12: 3435–3444. Synthetic oligonucleotides have been coupled directly to alkaline phosphatase [Jablonski, E., et al. (1986) Preparation of Oligodeoxynucleotide-Alkaline Phosphatase Conjugates and Their Use as Hybridization Probes. *Nucl. Acids Res.* 14: 6115–6128; and Li P., et al. (1987) Enzyme-linked Synthetic Oligonucleotide probes: Non-Radioactive Detection of Enterotoxigenic *Escherichia coli* in Faeca Specimens. *Nucl. Acids Res.* 15: 5275–5287].

Enzymes of interest as labels will typically be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol.

The oligonucleotide or polynucleotide acid probes of this invention can be included in a kit which can be used to rapidly determine the level of DPD DNA or mRNA in cells of a human or other mammalian sample. The kit includes all components necessary to assay for the presence of the DPD DNA or mRNA. In the universal concept, the kit includes a stable preparation of labeled probes specific for DPD nucleic acids, hybridization solution in either dry or liquid form for the hybridization of target and probe polynucleotides, as well as a solution for washing and removing undesirable and nonduplexed polynucleotides, a substrate for detecting the labeled duplex, and optionally an instrument for the detection of the label.

The probe components described herein include combinations of probes in dry form, such as lyophilized nucleic acid or in precipitated form, such as alcohol precipitated nucleic acid or in buffered solutions. The label can be any of the labels described above. For example, the probe can be biotinylated using conventional means and the presence of a biotinylated probe can be detected by adding avidin conjugated to an enzyme, such as horseradish peroxidase, which can then be contacted with a substrate which, when reacted with peroxidase, can be monitored visually or by instrumentation using a calorimeter or spectrophotometer. This labeling method and other enzyme-type labels have the advantage of being economical, highly sensitive, and relatively safe compared to radioactive labeling methods. The various reagents for the detection of labeled probes and other miscellaneous materials for the kit, such as instructions, positive and negative controls, and containers for conducting, mixing, and reacting the various components, would complete the assay kit.

2. Assays for Detecting DPD Nucleic Acid Deficiency

One embodiment of the invention provides assays for determining whether a patient is at risk of a toxic reaction to 5-fluorouracil, or suffers from a condition that is caused by inadequate levels of DPD (such as thymine uraciluria). The assay methods involve determining whether the patient is deficient in DPD nucleic acids. A deficiency can arise if the patient is lacking all or part of one or both copies of the DPD gene, or if the DPD gene is not expressed in the appropriate cells of the patient. Another potential cause of DPD deficiency that is detectable using the claimed invention is a nonsense or missense mutation in the DPD gene that results in an abnormal DPD polypeptide.

Assay test protocols for use in this invention are those of convention in the field of nucleic acid hybridization, and include both single phase, where the target and probe polynucleic acids are both in solution, and mixed phase hybridizations, where either the target or probe polynucleotides are fixed to an immobile support. The assay test protocols are varied and are not to be considered a limitation of this invention. A general review of hybridization can be had from a reading of *Nucleic Acid Hybridization*: A Practical Approach, Hames and Higgins, eds., IRL Press, 1985; and *Hybridization of Nucleic Acids Immobilized on Solid Supports*, Meinkoth and Wah (1984) *Analytical Biochemistry*, pp. 238, 267–284. Mixed phase hybridizations are preferred.

One potential cause of DPD deficiency is a deletion of all or part of one or more copies of the DPD gene in a patient's chromosomal DNA. To determine whether a patient lacks a gene that codes for DPD, the clinician can employ a Southern blot or other means suitable for detecting the presence of a specific nucleotide sequence in genomic DNA. A variety of methods for specific DNA and RNA measurement using nucleic acid hybridization techniques are known to those of skill in the art. See, e.g., Sambrook, supra. Briefly, the procedure for a Southern blot is as follows. Genomic DNA is isolated from a sample obtained from the patient. One can obtain DNA from almost any cellular tissue of the patient. The DNA is digested using one or more restriction enzymes, after which it is size-fractionated by electrophoresis through an agarose slab gel. The DNA is then immobilized by transfer from the gel to a membrane (commonly nylon or nitrocellulose).

If all or part of the DPD gene is missing from the patient's genomic DNA, the probe will not hybridize to the genomic DNA, or else will hybridize to a different-sized restriction fragment compared to the wild-type DPD gene. If a patient is heterozygous at the DPD locus, the clinician will observe either a reduced hybridization signal compared to wild-type (probe region deleted from one of the two alleles) or hybridization to two different-sized restriction fragments (part of one DPD gene deleted). If a sample from a patient lacks a gene that codes for DPD, the clinician should exercise extreme caution in using 5-FU as chemotherapy. A patient who is missing all or part of one or both DPD genes (e.g., either a heterozygote or homozygote for a defective DPD gene) is at risk of 5-FU toxicity or conditions such as thymine uraciluria that are due to inadequate levels of DPD activity.

DPD deficiency that results in 5-FU toxicity or thymine uraciluria might also result from insufficient DPD mRNA levels. The Northern blot is a particularly useful method for detecting DPD mRNA levels. By detecting DPD mRNA levels, rather than detecting the presence of the DPD gene, Northern blots permit quantitation of DPD gene expression. This facilitates identification of patients who are DPD deficient for any of several reasons. A homozygote in which both DPD alleles are deleted will produce no DPD mRNA, while a heterozygote will generally have an intermediate level of DPD mRNA compared to a patient who is homozygous wild type. A Northern blot also allows the clinician to identify patients who, although they carry DPD genes, have a lower than normal level of DPD gene expression. Such patients are also at risk of 5-FU toxicity and thymine uraciluria.

Suitable samples for detection of DPD mRNA include any cells from the patient that express the DPD gene. Preferably, the cells will be obtained from a tissue that has high levels of DPD activity. In humans, the liver and lymphocytes generally have the highest DPD activity, with other tissues having less activity [Naguib et al. (1985) *Cancer Res.* 45: 5405–5412]. Because lymphocytes are much easier to isolate from a patient than liver cells, lymphocytes are a preferred sample for detecting DPD mRNA according to the claimed invention. However, one can also detect DPD mRNA in other cell types, such as fibroblasts.

Suitable methods for Northern blots are described in, for example, Sambrook, supra. and Chomczynski and Sacchi (1987) *Anal. Biochem.* 162: 156–159. Briefly, RNA is isolated from a cell sample using an extraction solution that releases the RNA from the cells while preventing degradation of the RNA. A commonly-used extraction solution contains a guanidinium salt. The RNA is purified from the extraction solution, such as by phenol-chloroform extraction followed by ethanol precipitation. Optionally, one can separate the mRNA from ribosomal RNA and transfer RNA by oligo-dT cellulose chromatography, although such purification is not required to practice the claimed invention. The RNA is then size-fractionated by electrophoresis, after which the RNA is transferred from the gel to a nitrocellulose or nylon membrane. Labeled probes are used to ascertain the presence or absence of DPD-encoding mRNA.

If a sample from a patient has an insufficient amount of DPD nucleic acids, the patient is at risk of a toxic reaction to 5-FU, or is likely to suffer from thymine uraciluria or a related condition. Generally, an insufficient amount of DPD nucleic acids is less than about 70% of the normal amount of DPD nucleic acid, where "normal" refers to the amount of DPD nucleic acid found in the same amount of DNA or RNA from a sample that is not known to have a DPD deficiency. More typically, an amount of DPD that is less than about 50% of normal is indicative of an enhanced risk of 5-FU toxicity or thymine uraciluria.

Yet another potential cause of DPD deficiency in a patient is a missense or nonsense mutation in the DPD gene, or a mutation that interferes with mRNA processing. Our invention allows the clinician to detect these mutations. By choosing a probe that hybridizes to a mutant DPD gene, but not to the wild-type DPD gene (or vice versa), one can determine whether the patient carries an abnormal DPD gene that may result in inadequate expression of the DPD gene, or expression of an abnormal DPD enzyme that has less activity than the wild-type enzyme.

A variety of nucleic acid hybridization formats in addition to Northern and Southern blots are known to those skilled in the art. For example, common formats include sandwich assays and competition or displacement assays. Hybridization techniques are generally described in *"Nucleic Acid Hybridization, A Practical approach,"* Hames, B. D. and Higgins, S. J. (eds.), IRL Press, 1985; Gall and Pardue (1969) *Proc. Natl. Acad. Sci. USA.* 63: 378–383; and John et al. (1969) *Nature* 223: 582–587. These assays are sometimes preferred over classical Northern and Southern blots because of their greater speed and simplicity.

Sandwich assays are commercially useful hybridization assays for detecting or isolating nucleic acid sequences. These assays are easily automated, which results in a more cost-effective and sometimes more accurate assay. Sandwich assays utilize a "capture" nucleic acid that is covalently linked to a solid support, and a labelled "signal" nucleic acid that is in solution. The clinical sample provides the target nucleic acid. The "capture" nucleic acid and "signal" nucleic acid probe each hybridize to the target nucleic acid to form a "sandwich" hybridization complex. To be effective, the signal nucleic acid cannot hybridize to the capture nucleic acid.

One embodiment of this invention embraces a kit that utilizes the concept of the sandwich assay. This kit includes a first component for the collection of samples from patients, vials for containment, and buffers for the dispersement and lysis of the sample. A second component contains media in either dry or liquid form for the hybridization of target and probe polynucleotides, as well as for the removal of undesirable and nonduplexed forms by washing. A third component includes a solid support upon which is fixed or to which is conjugated unlabeled nucleic acid probe(s) that is(are) complementary to a DPD nucleic acid. In the case of multiple target analysis more than one capture probe, each specific for its own DPD nucleic acid target region, will be applied to different discrete regions of the dipstick. A fourth component contains labeled probe that is complementary to a second and different region of the same DPD nucleic acid strand to which the immobilized, unlabeled nucleic acid probe of the third component is hybridized.

No matter which assay format is employed, labelled signal nucleic acids are typically used to detect hybridization. Complementary nucleic acids or signal nucleic acids can be labelled by any one of several methods typically used to detect the presence of hybridized polynucleotides, as described above. The most common method of detection is the use of autoradiography with $^3$H, $^{125}$I, $^{35}$S, $^{14}$C, or $^{32}$P-labelled probes or the like. Other labels include ligands which bind to labelled antibodies, fluorophores, chemiluminescent agents, enzymes, and antibodies which can serve as specific binding pair members for a labelled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal. The label can also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. [Tijssen, P., "Practice and Theory of Enzyme Immunoassays," *Laboratory Techniques in Biochemistry and Molecular Biology*, Burdon, R. H., van Knippenberg, P. H., Eds., Elsevier (1985), pp. 9–20].

The sensitivity of the hybridization assays can be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems. Amplification methods permit one to detect the presence or absence of DPD nucleic acids using only a very small sample. Furthermore, amplification methods are especially amenable to automation.

One preferred method for detecting DPD deficiency is reverse transcriptase PCR (RT-PCR). Briefly, this method involves extracting RNA from the sample being analyzed, making a cDNA copy of the mRNA using an oligo-dT primer and reverse transcriptase, and finally amplifying part or all of the cDNA by PCR. For primers, one can use oligonucleotide primers that are complementary to the 5' and 3' sequences that flank the DNA region to be amplified. One can select primers to amplify the entire region that codes for a full-length DPD polypeptide, or to amplify smaller DNA segments that code for part of the DPD polypeptide, as desired. For human DPD analysis, suitable pairs of primers include: SEQ. ID Nos. 5 and 6, SEQ. ID Nos. 7 and 8, and SEQ. ID Nos. 9 and 10. A detailed example of RT-PCR analysis as used for detection of DPD deficiency is presented in Example 4 below.

An alternative means for determining the level at which a DPD gene is expressed is in situ hybridization. In situ hybridization assays are well known and are generally described in Angerer et al. (1987) Methods Enzymol. 152: 649–660. In an in situ hybridization assay, cells are fixed to a solid support, typically a glass slide. If DNA is to be probed, the cells are denatured with heat or alkali. The cells are then contacted with a hybridization solution at a moderate temperature to permit annealing of labeled probes specific to DPD-encoding nucleic acids. The probes are preferably labelled with radioisotopes or fluorescent labels.

C. Expression of Recombinant Dihydropyrimidine Dehydrogenase

The present invention also provides methods for expressing recombinant dihydropyrimidine dehydrogenase (DPD). These methods involve cloning the claimed isolated DPD cDNA into an appropriate expression vector, transforming the expression vector into a host cell, and growing the host cells under conditions that lead to expression of the DPD cDNA. Numerous expression systems are suitable for expression of cDNA encoding DPD. Because these basic techniques are known to those of skill in the art, no attempt is made here to describe in detail the various basic methods known for the expression of proteins in prokaryotes or eukaryotes.

In brief summary, the expression of natural or synthetic nucleic acids encoding DPD will typically be achieved by operably linking a DPD-encoding cDNA to a promoter that functions in the host cell of choice. Either constitutive or inducible promoters are suitable. This "expression cassette" is typically incorporated in an expression vector. The vectors contain regulatory regions that cause the vector to replicate autonomously in the host cell, or else the vector can replicate by becoming integrated into the genomic DNA of the host cell. Suitable vectors for both prokaryotes and eukaryotes are known to those of skill in the art. Typical expression vectors can also contain transcription and translation terminators, translation initiation sequences, and enhancers that are useful for regulating the amount of DPD expression. To obtain high level expression of a cloned gene, such as those polynucleotide sequences encoding DPD, it is desirable to construct expression vectors that contain, at minimum, a strong promoter to direct transcription, a ribosome binding site for translational initiation, and a transcription/ translation terminator. Expression vectors often contain control elements that permit the vector to replicate in both eukaryotes and prokaryotes, as well as selectable markers that function in each. See, e.g., Sambrook, supra., for examples of suitable expression vectors.

1. Expression in Eukaryotes

A variety of eukaryotic expression systems such as yeast, insect cell lines, bird, fish, and mammalian cells, are known to those of skill in the art. Eukaryotic systems, including yeast, mammalian, and insect, suitable for expressing DPD are discussed briefly below.

Synthesis of heterologous proteins in yeast is well known. *Methods in Yeast Genetics*, Sherman, F., et al., Cold Spring Harbor Laboratory, (1982) is a well recognized work describing the various methods available to produce the protein in yeast. Suitable vectors for expression in yeast usually have expression control sequences, such as promoters, including 3-phosphoglycerate kinase or other glycolytic enzymes, and an origin of replication, termination sequences and the like as desired. For instance, suitable vectors are described in the literature (Botstein, et al., 1979, *Gene,* 8:17–24; Broach, et al., 1979, *Gene,* 8:121–133). Several commercial manufacturers of molecular biology reagents sell expression vectors that are suitable for use in different eukaryotic host cells [See, e.g., product catalogs from Stratagene Cloning Systems, La Jolla Calif.; Clontech Laboratories, Palo Alto Calif.; Promega Corporation, Madison Wis.]. These vectors are used as directed by the manufacturers except for the modifications described below that are necessary for expression of DPD.

Two procedures are commonly used to transform yeast cells. The first method involves converting yeast cells into protoplasts using an enzyme such as zymolyase, lyticase or glusulase. The protoplasts are then exposed to DNA and polyethylene glycol (PEG), after which the PEG-treated protoplasts are then regenerated in a 3% agar medium under selective conditions. Details of this procedure are given in the papers by Beggs (1978) *Nature (London)* 275: 104–109 and Hinnen et al. (1 978) *Proc. Natl. Acad. Sci. USA* 75: 1929–1933. The second procedure does not involve removal of the cell wall. Instead the cells are treated with lithium chloride or acetate and PEG and put on selective plates [Ito et al. (1983) *J. Bact.* 153: 163–1681].

The DPD polypeptides, once expressed, can be isolated from yeast by lysing the cells and applying standard protein isolation techniques to the lysates. The monitoring of the purification process can be accomplished by using Western blot techniques, or radioimmunoassay or other standard immunoassay techniques.

Higher eukaryotes are also suitable host cells for expression of recombinant DPD. Again, previously described methods are suitable, except that the modifications described below are necessary for efficient expression of DPD. Expression vectors for use in transforming, for example, mammalian, insect, bird, and fish cells are known to those of skill in the art.

Mammalian cells are illustrative of the techniques used for expression of DPD in eukaryotic cells. Mammalian cells typically grow in the form of monolayers of cells, although mammalian cell suspensions may also be used. A number of suitable host cell lines capable of expressing intact proteins have been developed in the art, and include the HEK293, BHK21, and CHO cell lines, and various human cells such as COS cell lines, HeLa cells, myeloma cell lines, Jurkat cells, etc. Expression vectors for these cells can include expression control sequences, such as an origin of replication, a promoter (e.g., the CMV promoter, a HSV tk (thymidine kinase) promoter or pgk (phosphoglycerate kinase) promoter), an enhancer [Queen et al. (1986) *Immunol. Rev.* 89:49],and necessary processing information sites, such as ribosome binding sites, RNA splice sites, polyadenylation sites (e.g., an SV40 large T Ag poly A addition site), and transcriptional terminator sequences. Other animal cells useful for production of recombinant DPD are available, for instance, from the American Type Culture Collection Catalogue of Cell Lines and Hybridomas (7th edition, 1992), as well as from various commercial manufacturers of molecular biology reagents.

Insect cells are another eukaryotic system that is useful for expressing recombinant DPD protein. Appropriate vectors for expressing recombinant DPD in insect cells are usually derived from the SF9 baculovirus. Suitable insect cell lines include mosquito larvae, silkworm, armyworm, moth and Drosophila cell lines such as a Schneider cell line [See, Schneider J. (1987) *Embryol. Exp. Morphol.* 27:353–365].

Higher eukaryotic host cells, such as mammalian and insect cells, are rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and micro-injection of the DNA directly into the cells.

The transformed cells are cultured by means well known in the art. *Biochemical Methods in Cell Culture and Virology,* Kuchler, R. J., Dowden, Hutchinson and Ross, Inc (1977). The expressed polypeptides are isolated from cells grown as suspensions or as monolayers. The DPD polypeptides are recovered by well known mechanical, chemical or enzymatic means.

2. Expression in Prokaryotes

A variety of prokaryotic expression systems can be used to express recombinant DPD. Examples of suitable host cells include *E. coli,* Bacillus, Streptomyces, and the like. For each host cell, one employs an expression plasmids that contains appropriate signals that direct transcription and translation in the chosen host organism. Such signals typically include a strong promoter to direct transcription, a ribosome binding site for translational initiation, and a transcription/translation terminator. Examples of regulatory regions suitable for this purpose in *E. Coli* are the promoter and operator region of the *E. coli* tryptophan biosynthetic pathway as described by Yanofsky, C. (1984) *J. Bacteriol.* 158: 1018–1024 and the leftward promoter of phage lambda (pλ) as described by Herskowitz and Hagen (1980) *Ann. Rev. Genet.* 14: 399–445. Several commercial manufacturers of molecular biology reagents sell prokaryotic expression vectors that have been optimized for high levels of heterologous gene expression [See, e.g., product catalogs from Stratagene Cloning Systems, La Jolla Calif; Clontech Laboratories, Palo Alto Calif.; Promega Corporation, Madison Wis.]. These vectors are especially suitable for producing recombinant DPD, and are used as directed by the manufacturer, except that modifications to the growth medium are required for DPD expression, as described below.

Suitable expression vectors for use in prokaryotes typically contain a selectable marker that, when cells are grown under appropriate conditions, cause only those cells that contain the expression vector to grow. Examples of such markers useful in *E. coli* include genes specifying resistance to ampicillin, tetracycline, or chloramphenicol. See, e.g., Sambrook, supra. for details concerning selectable markers suitable for use in *E. coli*.

Overexpression of DPD causes elimination of pyrimidines from cells. Tis results in selection against cells that produce high levels of DPD invention provides methods to circumvent this problem. These methods involve adding uracil to the growth medium. Addition of other cofactors such as FAD and FMN also has a beneficial effect, although not as great as for uracil addition. For expression of DPD in *E. Coli*, for example, a preferred medium is Terrific Broth [Tartof and Hobbs (1987) Bethesda Research Labs FOCUS 9: 12] that contains 100 μgl/ml ampicillin or other antibiotic suitable for the selectable marker contained on the expression vector employed. To allow growth of cells that express DPD, the medium is typically supplemented with 100 μM uracil, and optionally 100 μM each of FAD and FMN, and 10 μM each of $Fe(NH_4)_2SO_4$ and $Na_2S$.

Recombinant DPD produced by prokaryotic cells may not necessarily fold into the same configuration as eukaryotically-produced DPD. If improper folding inhibits DPD activity, one can "refold" the DPD polypeptide by first denaturing the protein, and then allowing the protein to renature. This can be accomplished by solubilizing the bacterially produced proteins in a chaotropic agent such as guanidine HCl, reducing all the cysteine residues by using a reducing agent such as β-mercaptoethanol. The protein is then renatured, either by slow dialysis or by gel filtration. See, e.g., U.S. Pat. No. 4,511,503.

Detection of the expressed antigen is achieved by methods known in the art as radioimmunoassay, or Western blotting techniques or immunoprecipitation. Purification from *E. coli* can be achieved following procedures described in, for example, U.S. Pat. No. 4,511,503.

3. Purification of DPD Polypeptides

The DPD polypeptides produced by recombinant DNA technology as described herein can be purified by standard techniques well known to those of skill in the art. Typically, the cells are lysed (e.g., by sonication) and the protein is then purified to substantial purity using standard techniques such as selective precipitation with such substances as ammonium sulfate, column chromatography, immunopurification methods, and others. See, e.g., R. Scopes, *Protein Purification: Principles and Practice, Springer-Verlag*: New York (1982), which is incorporated herein by reference. For example, one can raise antibodies against the DPD polypeptides and use the antibodies for immunoprecipitation or affinity chromatography using standard methods.

If the DPD polypeptide is produced as a fusion protein, in which the DPD moiety is fused to non-DPD amino acids, the desired polypeptide can be released by digestion with an appropriate proteolytic enzyme.

D. Use of DPD nucleic acids as selectable markers

Another aspect of the claimed invention is the use of a DPD nucleic acid as a selectable marker that is effective in both prokaryotes and eukaryotes. Selectable markers are genes that, when present in a cloning vector, produce a gene product that enables cells containing the vector to grow under conditions that prevent cells lacking the vector from growing. In contrast to the selectable markers of the invention, most selectable markers function only in one or the other of eukaryotes and prokaryotes, not in both. Thus, cloning vectors that are intended for propagation in both types of organisms usually require two different selectable markers.

The claimed selectable markers are DPD-encoding nucleic acids. Cells that express these nucleic acids are resistant to 5-FU. 5-fluorouracil, which is toxic to both prokaryotic and eukaryotic cells, is degradatively inactivated by DPD. Therefore, one can select cells that contain a DPD nucleic acid that is operably linked to a promoter simply by growing the cells in the presence of 5-FU. To practice the invention, one operably links the DPD nucleic acid to a promoter that functions in the host cell of interest. Suitable promoters and other control signals are described above. In a preferred embodiment, the DPD nucleic acid is integrated into an expression cassette that functions in both prokaryotes and eukaryotes. One example of such a bifunctional expression cassette is the ZAP Express™ expression cassette (Stratagene, La Jolla Calif.), which is described in U.S. Pat. No. 5,128,256. The DPD nucleic acid is inserted into the multiple cloning site which is downstream of a tandem array that includes both prokaryotic and eukaryotic transcription and translation regulatory sequences.

To determine appropriate growth conditions for using the DPD selectable marker, one first tests the untransformed host cells of interest for ability to grow in medium containing various amounts of 5-FU. A 5-FU concentration that results in complete or nearly complete inhibition of host cell growth is then employed in the medium used to select transformants. The amount of 5-FU required may vary depending on the particular medium used, the host cells, and whether the cells are grown in liquid culture or on a solid medium such as agar.

EXAMPLES

Example 1:

Cloning and Characterization of Pig and Human DPD cDNAs

In this Example, we describe the cloning and characterization of cDNAs for pig and human dihydropyrimidine dehydrogenases.

MATERIALS AND METHODS

We isolated total RNA from frozen pig liver using the method of Chirgwin et al (1979) *Biochemistry* 18: 5294–5299, except that we used CsTFA (Pharmacia, Inc., Milwaukee, Wis.) instead of CsCl. We extracted the RNA twice with phenol-chloroform emulsion and then ethanol precipitated the RNA prior to use. Next, we isolated poly(A) RNA by oligo (dT)-cellulose chromatography [Aviv and Leder (1977) *Proc. Nat'l. Acad. Sci. USA* 69: 1408–1412] and used it as a template for synthesis of cDNA. We used oligo-dT as a primer, and extended the primer using reverse transcriptase. Then, we made the cDNA double-stranded and cloned it into λgt24A using a kit supplied by Gibco BRL Life Technologies, Inc., Gaithersburg, Md. The DNA was packaged using the λ packaging system from Gibco BRL. We plated the phage particles in *Escherichia coli* Y1090r.

To identify plaques that express pig DPD, we screened the library using a polyclonal antibody against pig DPD [Podschun et al. (1989) *Eur. J. Biochem.* 185: 219–224]. We obtained a partial cDNA that we used to rescreen the library in *E. Coli* Y1088 by plaque hybridization. This yielded a cDNA that contained the complete DPD reading frame. We subcloned the cDNA into the NotI and SalI sites of the plasmid vector pSport (Gibco BRL).

To clone the human DPD cDNA, we used a fragment of the pig cDNA that includes most of the coding region to screen previously amplified human liver cDNA libraries that had been prepared in λgt11 [Yamano et al. (1989) *Biochemistry* 28: 7340–7348]. We isolated the human DPD cDNA as three overlapping fragments, which we subcloned into the Eco RI site of pUC18. The three fragments were joined together using overlapping Cla I sites in pUC18. We then determined the complete sequences of pig and human DPD cDNAs using an Applied Biosystems 373A DNA sequencer, synthetic primers, and fluorescent dye terminator chemistry as described by the manufacturer. The oligonucleotide primers were synthesized using a CENTRICON 10™ filter (Millipore Corp.). Each base was determined at least once on both strands. The DNA and deduced amino acid sequences were analyzed using MacVector sequence analysis software (International Biotechnologies, Inc., New Haven, Conn.).

RESULTS

We isolated partial pig cDNAs by screening 1×10⁶ plaques from an unamplified λgt22A library. After verification by sequencing, we used a partial cDNA to rescreen 500,000 plaques. Four cDNAs were isolated which contained inserts of about 4.5 kb. We completely sequenced one of these and found that it encompassed the full coding region of the protein FIGS. 2A-1.FIG. 2A., and FIG. 2B. The deduced amino acid sequence of the amino terminal region agrees with the amino acid sequence determined from the pig enzyme [Podschun et al. (1 989) *Eur. J. Biochem.* 185: 219–224. A number of segments of amino acids previously sequenced were found in the cDNA-deduced amino acid sequence (FIG. 3, underlined). These were determined by cyanogen bromide cleavage (residues 117–127) and trypsin cleavage (residues 260–277; 308–315; 656–682; 904–913) followed by HPLC separation and sequencing (data not shown). The first residue of the amino terminal portion of the 12,000 dalton cleavage fragment from the pig DPD is shown by a vertical arrow at residue 904. These data establish the pig DPD open reading frame of 1025 amino acids.

The nucleotide sequence of the human DPD is shown in FIGS. 1A-1., FIG.1A-2. through FIG. 1B. The deduced amino acid sequence of the human DPD is identical to that of the pig DPD, except where indicated in FIG. 3. The calculated molecular weights are 111,416 and 111,398 daltons for pig and human DPD, respectively. The poly(A) addition sequence of AAATAAA is found 17 bp upstream of a putative poly(A) tract cloned in the cDNA. This 3' -untranslated region was not isolated in the human cDNA clones.

The cDNA-derived protein sequences revealed the presence of a number of putative binding sites for known DPD cofactors. Recent EPR measurements on DPD from *Alcaligenes eutrophus* confirmed the existence of FMN, iron, and acid-labile sulfide, the latter two of which are indicative of iron sulfur clusters [Schmitt et al. (1994) *J. Inorg. Biochem.* (in press). The C-terminal 12 kDa peptide fragment purified from the pig DPD shows absorbance in the 500–600 nm region and contains eight iron and eight acid-labile sulfides (Podschun et al. (1 989), supra.]. The binding site of iron-sulfur clusters contain Cys residues, a large number of which are found in the N-terminal half of the protein. However, these do not exhibit the typical motif pattern seen in other well-characterized iron sulfur-containing proteins. In the C-terminal region of pig and human DPD are typical motifs CXXCXXCXXXCX (SEQ ID No. 11) and CXXCXXCXXXCP (SEQ ID No. 12) for [4Fe-4S] clusters [Dupuis et al. (1991) *Biochemistry* 30: 2954–2960] between residues 953 and 964 and residues 986 and 997, respectively. These lie within the 12 kDa iron-sulfur cluster-containing peptide [Podschun et al. (1989), supra.]. No other [4Fe-4S] clusters were detected; however, other types of iron sulfur clusters such as [2Fe-2S] might be possible.

A typical NADPH binding motif VXVXGXGXXGXXX-AXXA (SEQ ID No. 13) [Wierenga et al. (1985) *Biochemistry* 24: 1346–1357] begins with V-335, except that the Gly at position 10 is an Ala in pig and human DPD. A motif for FAD binding, TXXXXVFAXGD [Eggink et al. (1990) *J. Mol. Biol.* 212: 135-142], is in the N-terminal region starting with T-471 and ending with D-481.

We elucidated the putative uracil binding site of DPD by incubating DPD in the presence of 5-iodouracil, a suicide inactivator of the bovine enzyme, and sequencing the modified chymotryptic peptide [Porter et al. (1991) *J. Biol. Chem.* 266: 19988–19994]. The corresponding sequence obtained is located between G-661 and R-678 in the primary protein sequence. Thus, the order of the functional domains of DPD is, from the N-terminus, NADPH/NADP-FAD-uracil-[4Fe-4S].

Example 2:
Chromosome localization of the DPD gene

We localized the DPD gene to a specific human chromosome using a somatic cell hybrid strategy. Human-mouse and human-hamster cell lines were generated and characterized as described by McBride et al. [(1 982a) *Nucl. Acids Res.* 10: 8155–8170; (1982b) *J. Exp. Med.* 155: 1480–1490; (1982c) *Proc. Nat'l. Acad. Sci. USA* 83: 130–134]. The human chromosome of each call line was determined by standard isoenzyme analyses as well as by Southern analysis with probes from previously localized genes, and frequently, by cytogenetic analysis. Southern blots of hybrid cell DNA restriction digests on positively charged nylon membranes were prepared after (0.7%) agarose gel electrophoresis and hybridized at high stringency with $^{32}$P-labeled probes under conditions allowing no more than 10% divergence of hybridizing sequences.

We localized the DPD gene to human chromosome 1 by Southern analysis of a panel of human/rodent somatic cell hybrid DNAs digested with Eco RI using a 3' coding cDNA fragment as probe (Table 1). The gene segregated discordantly ($\geq 14\%$) with all other human chromosomes. The 3' probe identified a series of bands in human DNAs ranging in size from 0.8 to 1.5 kb. All hybridizing human bands appeared to cosegregate indicating that these bands were all present on the same chromosome. We then sub-localized the gene on chromosome 1 by analysis of hybrids containing spontaneous breaks and translocations involving this chromosome. One human/hamster hybrid with a break between NRAS (1p12) and PGM1 (1p22) retained the telomeric portion of the chromosome 1 short arm but the DPD gene was absent from this hybrid. Another human/hamster hybrid and a human/mouse hybrid each retained all, or nearly all, of the short arm of chromosome 1 including NRAS and all other short arm markers but all long arm markers were absent including a cluster of genes at 1q21 (trichohyalin, loricrin, and filaggrin); the human DPD gene was present in both of these hybrids. Finally, one additional human/hamster hybrid retained a centromeric fragment of chromosome 1 with the breakpoints on the long arm and short arm proximal to 1q21 and proximal to 1p31, respectively, and human DPD was present in this hybrid. These results indicate that the DPD gene can be sublocalized to the region 1 p22-q21.

We confirmed these results by Southern analysis of the same panel of hybrids with a DPD 5' cDNA probe which detected 1.5, 5.0, 8.7,and 11.6 kb bands in human EcoRI digests. Both probes were used to examine DNAs from ten unrelated individuals separately digested with 12 different restriction enzymes for RFLPs. However, no polymorphisms were detected. A large number of hybridizing bands were detected with both DPD probes and these bands cosegregated indicating that they are all localized to the centromeric region of human chromosome 1 (i.e., 1p22-q21). A number of cross-hybridizing hamster and mouse bands were also identified with these probes. These results are consistent with the interpretation that there may be a single reasonably large gene (spanning at least 80 kb) in each of these species, and all hybridizing bands arise from a single gene.

However, we currently cannot exclude the possibility that the many hybridizing bands arise from a cluster of tandemly linked genes.

Recently, the human DPD gene (named "DPYD" by the human gene nomenclature committee) was more precisely mapped to 1p22 [Takai et al. (1994) (submitted for publication)].

Example 3:
Expression of Pig DPD in *E. coli*

In this Example, we demonstrate the heterologous expression of a DPD polypeptide in a prokaryotic organism. Because large amounts of DPD protein are toxic to the host cells under normal growth conditions, additional components such as uracil are required in the medium.

METHODS

Construction of the Expression Plasmid. We constructed an expression plasmid by subcloning the pig DPD cDNA into the vector pSE420 (Invitrogen Corp., San Diego, Calif.). The cDNA contains an Nco I site coincident with the start codon (CCATGG) which was joined to the Nco I site in the vector that is in frame with the bacterial initiator Met. The pig DPD cDNA was inserted into pSE420 as an NcoI/Af/lll fragment from the pSPORT vector in which the pig DPD cDNA had previously been subcloned.

DPD Expression in *Escherichia coli*. For each expression experiment, a single colony from a freshly made transformation of DH-5α cells with the expression vector was inoculated in LB broth and grown to stationary phase. An aliquot from this culture was used to inoculate 250 ml of terrific broth containing 100 μg/ml ampicillin and supplemented with 100 μM of each FAD and FMN, 100 μM uracil and 10 μM each of $Fe(NH_4)_2(SO_4)$ and $Na_2S$. Following a 90 min incubation at 29° C., we induced the trp-lac promoter in the expression vector by the addition of 1 mM isopropyl-β-d-thiogalacto-pyranoside (IPTG) and the culture was incubated for an additional 48 h.

The cells were then sedimented, washed twice with 250 ml of phosphate buffered saline (PBS) and resuspended in 45 ml of 35 mM potassium phosphate buffer (pH 7.3) containing 20% glycerol, 10 mM EDTA, 1 mM DTT, 0.1 mM PMSF and 2 μM leupeptin. The cell suspension was lysed at 4° C. with four 30 sec bursts of a Heat Systems sonicator model W 225-R at 25% of full power (Heat Systems-Ultrasonics, Inc., Plain View N.Y.). The resultant lysate was centrifuged at 100,000×g for 60 min at 4° C. We then slowly added solid $(NH_4)_2SO_4$ to the supernatant at 4° C. with gentle stirring to give a final concentration of 30% saturation. The precipitate was sedimented and the pellet containing expressed DPD was resuspended in 5 ml of 35 mM potassium phosphate buffer (pH =7.3) containing 1 mM EDTA/1 mM DTT and 0.1 mM PMSF. The protein solution was dialyzed at 4° C. for 36 h against 3 changes of 4 liters each of buffer and stored at -70° C. until further use.

Catalytic assay. DPD activity was determined at 37° C. by measuring the decrease in absorbance at 340 nm associated with the oxidation of NADPH to $NADP^+$. The reaction mixture contained 28 mM potassium phosphate buffer (pH 7.3), 2 mM $MgCl_2$, 1 mM DTT, 60 μM NADPH and the expressed DPD in a final volume of 1 ml. The measurements were carried out using an Aminco DW-2000 double beam spectrophotometer using a blank that contained the complete reaction mixture except substrate. The reactions were initiated by addition of substrate (uracil, 5-fluorouracil or thymine). The catalytic activity was calculated as μmole of NADPH oxidized per minute and per mg of expressed DPD. Protein quantities were determined using the bicinchronic (BCA) procedure from Pierce Chemical Co., Rockford, Ill.) following the manufacturer's directions.

Analysis of cDNA-Expressed DPD Protein. SDS-polyacrylamide gel electrophoresis was carried out following the method of Laemmli [(1970) *Nature* 227: 680–685] using 8% acrylamide slab gels. The SDS-page gels were transferred to a nitrocellulose membrane by electroblotting for 90 min at 1.5 $mA/cm^2$ [Towbin et aL (1979) *Proc. Nat'l Acad. Sci. USA* 76: 4350–4354]. The membranes were blocked at room temperature using phosphate buffered saline (PBS) containing 0.5% Tween 20 and 3% skim milk. After blocking, the membranes were incubated for 4 h at room temperature with rabbit anti pig DPD polyclonal antibody dilute 200-fold in PBS. The membranes were washed three times in PBS containing 0.5% Tween 20 and rinsed twice with PBS prior to addition of alkaline phosphatase-labeled goat anti-rabbit IgG. Incubation was continued for 90 min and the membranes were developed using the reagent BCIP/NBT (Kikegaard & Perry Labs. Gaithersburg, Md.).

RESULTS

The pig DPD was expressed in bacteria using the vector pSE 420 which has a trp-lac promoter that is inducible by isopropyl-β-d-thiogalacto-pyranoside (IPTG). Optimal expression was obtained when cells were grown at a temperature between 26° C. and 30° C. Growth at higher temperatures resulted in aggregation of the protein in inclusion bodies. A number of cofactors known to be associated with the enzyme were added to the medium; the most critical was uracil which resulted in a greater than five-fold increase in DPD expression levels, compared to cells grown in unsupplemented medium.

The recombinantly expressed DPD enzyme comigrated with the intact 102 kDa DPD purified from pig liver and reacted with rabbit polyclonal antibody [Podschun et al. (1989) supra.] directed against the pig enzyme. DPD protein was undetectable in cells containing the expression vector without the DPD cDNA insert. The DPD purified from pig liver frequently has a second higher mobility band of about 12 kDa that results from a protease-labile site that liberates the iron sulfur- containing C-terminal fragment [Podschun et al. (1989) supra.].

The bacterially-expressed enzyme is produced intact and could be significantly purified away from other *E. coli* proteins by a single ammonium sulfate fractionation. By use of the purified pig DPD as a standard, we estimate that 50 to 100 mg of DPD were produced per liter of *E. coli* culture.

We tested the recombinantly expressed DPD enzyme for ability to metabolize typical DPD substrates such as uracil, thymine and 5-fluorouracil. Kinetic studies revealed that the recombinant DPD follows the ping pong reaction mechanism as previously shown for purified pig DPD [Podschun et al. (1989), supra.]. The Km's of the recombinant DPD are of similar magnitude to the values published for the purified pig [Podschun et al. (1989), supra.], human [Lu et al. (1992) *J. Biol. Chem.* 267: 17102–17109] and rat DPD enzymes [Fujimoto et aL (1991) *J. Nutr. Sci. Vitaminol.* 37: 89–98]. The Vmax values of expressed DPD were about three to five-fold lower than the purified pig enzyme reflecting the fact that the expressed DPD was only partially purified. However, these data establish that the expressed enzyme reflects the properties of the purified pig liver DPD. Thus, *E. coli* should prove useful for examining any enzymatic variants obtained through screening DPD-deficient individuals and for preparing large amounts of intact holoenzyme for physico-chemical analysis.

Example 4:
Identification of mutations within DPYD gene

In an effort to understand the genetic basis for DPD deficiency, we analyzed a Dutch family that included a DPD-deficient individual. We determined the phenotype for thymine metabolism and related it to the DPD protein content in fibroblasts. Then we identified the genetic defect using RT-PCR and found that the deficiency was due to a homozygous deletion in the DPD mRNA. The deleted portion corresponded to an exon in the DPYD gene. This phenotype/genotype relationship accounts for the DPD metabolic disorder in the patient. Additionally, we confirmed an autosomal recessive pattern of inheritance for DPD deficiency.

METHODS

Isolation of RNA. RNA was isolated from cultures of human fibroblast corresponding to all five subjects used in this study by the guanidinium thiocyanate phenol-chloroform method [Chomczynski and Sacchi (1987) *Anal. Biochem.* 162: 156–159]. The RNA was dissolved in water and stored at −80° C. until further use.

RT-PCR. cDNA was synthesized by reverse transcription from total RNA isolated from cultured fibroblast. About 1 μg of total RNA was mixed with oligo-dT primers and incubated at 65° C. for 15 min to denature secondary structure in the template. The primed RNA was incubated for 60 min at 40° C. in 20 μl of a reaction mixture containing 100 mM Tris-HCl (pH 8.3), 40 mM KCl, 10 mM $MgCl_2$, 50 μM spermidine, 1 00 mM dNTPs, 4 mM sodium phosphate, 0.5 units placental RNase inhibitor and 0.5 units of AMV reverse transcriptase (Invitrogen, Calif.). The synthesis reaction was repeated once by the addition of 0.5 units of fresh reverse transcriptase. The cDNA was made double stranded by PCR without further purification. The coding region of the cDNA was amplified in three fragment with the primer pairs indicated in Table 1.

TABLE 1

Primer pairs for RT-PCR analysis of human DPD cDNA (hDPD).

| Fragment amplified | Location in hDPD cDNA (nucleotides) | Primer sequence | SEQ. ID No. |
|---|---|---|---|
| 1.5 kb | RTF1.36 - 55 | 5'GCAAGGAGGGTTTGTCACTG3' | 5 |
|  | RTR1:1558 - 1536 | 5'CCGATTCCACTGTAGTGTTAGCC3' | 6 |
| 906 bp | H13:1539 - 1558 | 5'TAACACTACAGTGGAATCGG3' | 7 |
|  | RTR4:2445 - 2426 | 5'AAATCCAGGCAGAGCACGAG3' | 8 |
| 919 bp | RTR5:2424 - 2447 | 5'TGCTCGTGCTCTGCCTGGATTTCC3' | 9 |
|  | RTR5:3343 - 3320 | 5'ATTGAATGGTCATTGACATGAGAC3' | 10 |

We carried out PCR in 50 μl of a reaction mixture consisting of 10 mM Tris-HCl (pH 8.3), 50 mM KCl, 2.5 mM $MgCl_2$, 0.5 mM dNTPs, 1 μM primers and 2.5 units Taq polymerase (Perkin-Elmer Cetus). Thirty cycles were used, each cycle consisted of denaturing at 96° C. for 1 min, annealing at 55° C. for 1 min and extending at 72° C. for 2 min. The amplified products were extracted with 1 volume chloroform and purified by filtration through Centricon™ 100 filter units (Amicon, Inc. Beverly Wash.). Typically, we used one fifth of the PCR product for DNA sequence analyses with an Applied Biosystems 373A automated sequencer and fluorescent dye-deoxy terminator chemistry. We elucidated appropriate primers for DNA sequencing from the DPD cDNA sequence disclosed herein and synthesized the primers using an Applied Biosystems 394 DNA & RNA synthesizer. Sequence data have been analyzed using MacVector™ sequence analysis software (International Biotechnologies).

PCR Product Analysis and Southern Blots. We analyzed the PCR fragments by electrophoresis through a 1 % agarose gel in the presence of ethidium bromide. Prior to Southern blotting, the gels were depurinated by a 20 min incubation in 200 mM HCl, after which we denatured the DNA by a 20 min incubation in 0.5M NaOH. The DNA was transferred to Gene Screen Plus™ membranes (New England Biolabs) overnight in 0.5M NaOH as the transfer solution. We fixed the DNA by baking at 80° C., prehybridized at 65° C. for 3 h in a solution containing 6×SSC, 1×Denhardt's reagent, 0.5% sodium dodecyl sulfate and 0.2 mg/ml sonicated salmon sperm DNA. We then hybridized overnight at 65° C. in the same solution containing $1.5 \times 10^6$ cpm/ml of $^{32}P$ random priming labelled human DPD cDNA. After washing at 65° C. for 20 min in 2×SSC, 0.5% SDS and 45 min 0.1×SSC, 0.5% SDS at 65° C., the membranes were exposed to X-ray film (Eastman Kodak, Co.) at −80° C. for 30 min.

Western Immunoblots. We carried out SDS-PAGE gel electrophoresis using the method of Laemmli (1970) *Nature* 227: 107–111. The gels were transferred to nitrocellulose by semi-dry electroblotting for 90 min at 1.5 mA/cm$^2$. We detected DPD polypeptides using rabbit anti-pig DPD primary antibody and the enhanced chemiluminescence (ECL) detection method (Amersham Corp.), following the directions supplied by the manufacturer. Protein concentrations were determined using the bicinchronic acid procedure (Pierce Chemical Co., Rockford, Ill.) using bovine serum albumin as standard.

Catalytic Activity. We measured DPD activity in human fibroblast extracts by HPLC using a modification of the method described by Tuchman et al. (1989) *Enzyme* 42: 15–24, using [$^{14}$C]-thymine as substrate.

RESULTS

Clinical evaluation. We have studied the genetic basis for the complete lack of DPD activity in one of the members of the pedigree shown in FIG. 4. The patient (subject 4) was admitted to the hospital at the age of 25 months with bilateral microphtalmia, iris and choroidea coloboma, and nystagmus, in addition to a gradually increasing psychomotor retardation. However, no growth retardation or neurological abnormalities were detected. All other members of the pedigree were healthy and showed no abnormalities. The patient was diagnosed to have severe thymine-uraciluria. Skin biopsies were taken in order to establish fibroblast cultures that were used in this study.

Figure 5:
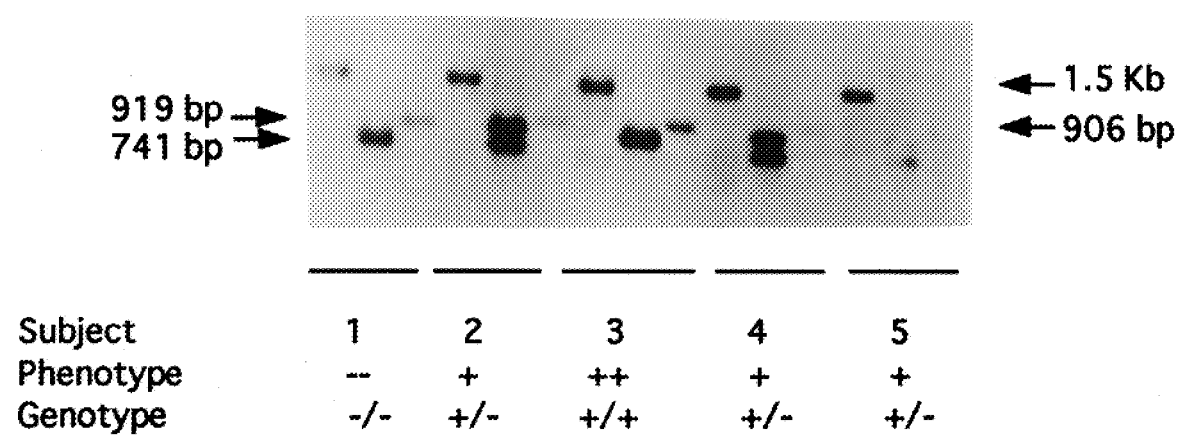
FIG. 5 shows a Southern blot of the products from reverse transcriptase PCR amplified cDNA for the subjects shown in FIG. 4. The 906 and 741 bp bands correspond to the wild-type and the deleted DPD cDNA fragments, respectively. "+" signifies the presence of the wild-type allele and "−" signifies the presence of the mutant allele.
Figure 6:
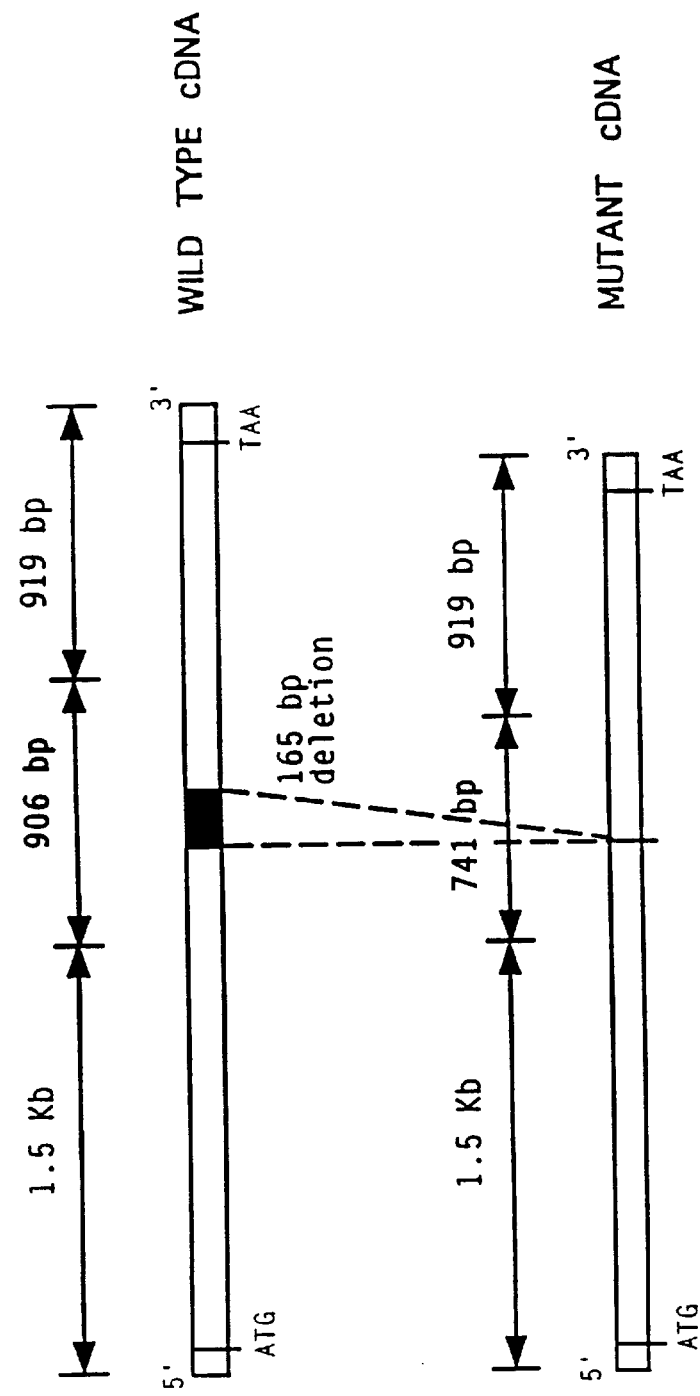
FIG. 6 is a schematic of the wild-type and mutant DPD cDNAs. Numbers above the cDNA graphical representation represent nucleotide positions. Start and stop codons are indicated.
Figure 7:
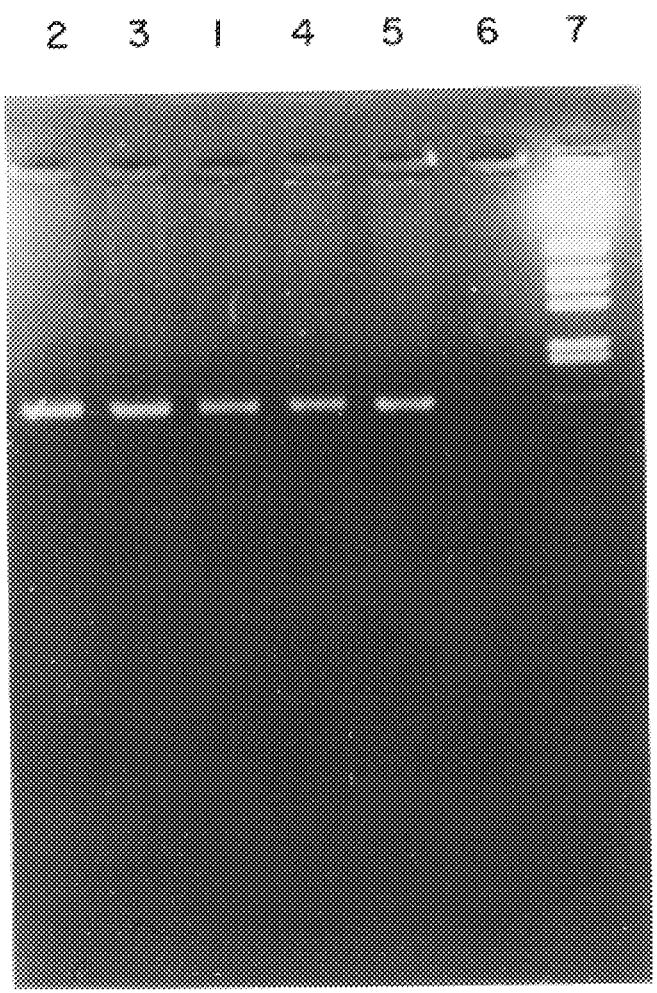
FIG. 7 is a PCR analysis of the DPD cDNA deletion found in the subject family. The numbers of the subjects correspond to those indicated in FIG. 4. Lane 6 is a negative control (no template present) and Lane 7 contains a 1 kb marker ladder (GIBCO BRL).

RT-PCR analysis of the DPD mRNA in cultured fibroblasts. Fibroblast total RNA from every subject was subjected to RT-PCR. The PCR products were hybridized with the [$^{32}$P]-labelled human DPD cDNA and the result is shown in FIG. 5. The coding sequence of the DPD cDNA was fully amplified in three fragments that span 1500, 906 and 919 bp. All the fragments are present every subject, including the patient. The 1500 and 919 bp fragments were constant in all subjects. However, the 906 bp fragment was found in only certain subjects and was in linkage disequilibrium with a fragment of 741 bp. The latter was homozygous in the deficient patient and found together with the predicted normal size fragment in both parents. One sibling was heterozygous and another was homozygous for the normal allele. To confirm the possibility of a deletion in the mRNA-derived cDNA associated with the DPYD alleles of these subjects, we sequenced the PCR fragments using nested primers and found that the 741 originated from the 906 bp fragment by a deletion of 165 bp. A schematic representation showing the structure of both mRNAs is shown in FIG. 6. Through partial sequencing of the DPYD gene, we found that the deletion present in the mRNA was coincident with a splicing site located in the genomic sequence of the DPYD gene that comprises a 165 bp exon. We have also found that the DNA corresponding to the deletion is present in the genomic DNA from the fibroblast cell lines since, as shown in FIG. 7, the deleted cDNA sequence can be amplified by PCR from the genomic DNA in the patient, as well as from genomic DNA from other members of the family. These results indicate that the variant transcript is not the result of a large deletion containing the missing exon, but rather is the result of a mutation that causes incorrect splicing.

Catalytic activity and DPD protein content. DPD activities from the fibroblast cell lines were determined by HPLC (Table I). The maximum activity, 1 nmol h$^{-1}$ mg protein$^{-1}$, corresponds to subject 3 that was homozygous for the normal mRNA. The parents and another sibling (subjects 4, 5, and 2) present a lower value and the patient, subject 1, had background activity. It should be noted that the DPD activity obtained in human fibroblast is about 8y obtained in human fibroblast is about 8–9 times lower than the equivalent activity in DPD from human lymphocytes.

To determine if the DPD protein content in our subjects follows a pattern similar to that of the catalytic activity, we measured fibroblast DPD protein by Western blots. DPD protein was not detectable in the patient, but was found in two other members of his family (subjects 2 and 4 in FIG. 4) who were analyzed for comparison.

The catalytic activity pattern correlates with the DPD protein content for the different subjects. As expected, the patient with only background DPD activity in his fibroblast has no detectable DPD band in the Western blot when using an anti-pig DPD polyclonal antibody, suggesting a complete lack of DPD protein. It is interesting to note that even though the DPD protein is defective and does not accumulate in the cell, the DPD mRNA is present, indicating that the defective mRNA is not particularly unstable as compared to the mRNA encoding the active DPD protein.

In conclusion, this study established with certainty that thymine uraciluria is due to a mutation in the DPYD gene.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated by reference.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An isolated nucleic acid encoding a dihydropyrimidine dehydrogenase (DPD) protein wherein the nucleic acid selectively hybridizes, under stringent hybridizing conditions, to a second nucleic acid consisting of the nucleotide sequence of Seq. ID No. 1 or Seq. ID No. 3 or an isolated nucleic acid which encodes seq ID Nos:2 or 4.

2. The nucleic acid of claim 1 wherein the nucleic acid is of human origin.

3. The nucleic acid of claim 2 wherein the nucleic acid consists of the nucleotide sequence of Seq. ID. No.1.

4. The nucleic acid of claim 1 wherein the nucleic acid is of pig origin.

5. The nucleic acid of claim 4 wherein the nucleic acid consists of the nucleotide sequence of Seq. ID. No.3.

6. The nucleic acid of claim 1 wherein the nucleic acid is full-length.

7. An isolated oligonucleotide probe that selectively hybrids, under stringent hybriding conditions, to SEQ ID NO:1 or 3, wherein said probe does not selectively hybridize, under stringent hybridizing conditions, to a non-DPD nucleic acid.

8. An oligonucleotide probe of claim 7 that is between about 10 and 100 nucleotides in length.

9. An expression vector comprising a selectable marker, wherein the selectable marker is a nucleic acid of claim 1.

10. An expression vector as in claim 9 wherein the selectable marker is operably linked to at least one promoter.

11. An expression vector as in claim 10 wherein the promoter functions in a eukaryote.

12. An expression vector as in claim 10 wherein the promoter functions in a prokaryote.

13. An expression vector as in claim 10 wherein the selectable marker is operably linked to both a prokaryotic and a eukaryotic promoter.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 3957 base pairs
( B ) TYPE: nucleic acid
( C ) STRANDEDNESS: single
( D ) TOPOLOGY: linear ( i i ) MOLECULE TYPE: cDNA ( i x ) FEATURE:
    ( A ) NAME/KEY: CDS
    ( B ) LOCATION: 88..3162

( i x ) FEATURE:
    ( A ) NAME/KEY: misc_feature
    ( B ) LOCATION: 1..3957
    ( D ) OTHER INFORMATION: /product= "Human DPD"

( x i ) SEQUENCE DESCRIPTION: SEQ ID NO:1:

```
AGACACGCTG TCACTTGGCT CTCTGGCTGG AGCTTGAGGA CGCAAGGAGG GTTTGTCACT        60

GGCAGACTCG AGACTGTAGG CACTGCC ATG GCC CCT GTG CTC AGT AAG GAC          111
                             Met Ala Pro Val Leu Ser Lys Asp
                              1                   5

TCG GCG GAC ATC GAG AGT ATC CTG GCT TTA AAT CCT CGA ACA CAA ACT        159
Ser Ala Asp Ile Glu Ser Ile Leu Ala Leu Asn Pro Arg Thr Gln Thr
        10              15                  20

CAT GCA ACT CTG TGT TCC ACT TCG GCC AAG AAA TTA GAC AAG AAA CAT        207
His Ala Thr Leu Cys Ser Thr Ser Ala Lys Lys Leu Asp Lys Lys His
 25                  30                  35                  40

TGG AAA AGA AAT CCT GAT AAG AAC TGC TTT AAT TGT GAG AAG CTG GAG        255
Trp Lys Arg Asn Pro Asp Lys Asn Cys Phe Asn Cys Glu Lys Leu Glu
                 45                  50                  55

AAT AAT TTT GAT GAC ATC AAG CAC ACG ACT CTT GGT GAG CGA GGA GCT        303
Asn Asn Phe Asp Asp Ile Lys His Thr Thr Leu Gly Glu Arg Gly Ala
             60                  65                  70

CTC CGA GAA GCA ATG AGA TGC CTG AAA TGT GCA GAT GCC CCG TGT CAG        351
Leu Arg Glu Ala Met Arg Cys Leu Lys Cys Ala Asp Ala Pro Cys Gln
         75                  80                  85

AAG AGC TGT CCA ACT AAT CTT GAT ATT AAA TCA TTC ATC ACA AGT ATT        399
Lys Ser Cys Pro Thr Asn Leu Asp Ile Lys Ser Phe Ile Thr Ser Ile
     90                  95                 100

GCA AAC AAG AAC TAT TAT GGA GCT GCT AAG ATG ATA TTT TCT GAC AAC        447
Ala Asn Lys Asn Tyr Tyr Gly Ala Ala Lys Met Ile Phe Ser Asp Asn
105                 110                 115                 120

CCA CTT GGT CTG ACT TGT GGA ATG GTA TGT CCA ACC TCT GAT CTA TGT        495
Pro Leu Gly Leu Thr Cys Gly Met Val Cys Pro Thr Ser Asp Leu Cys
                125                 130                 135

GTA GGT GGA TGC AAT TTA TAT GCC ACT GAA GAG GGA CCC ATT AAT ATT        543
Val Gly Gly Cys Asn Leu Tyr Ala Thr Glu Glu Gly Pro Ile Asn Ile
            140                 145                 150

GGT GGA TTG CAG CAA TTT GCT ACT GAG GTA TTC AAA GCA ATG AGT ATC        591
Gly Gly Leu Gln Gln Phe Ala Thr Glu Val Phe Lys Ala Met Ser Ile
        155                 160                 165

CCA CAG ATC AGA AAT CCT TCG CTG CCT CCC CCA GAA AAA ATG TCT GAA        639
Pro Gln Ile Arg Asn Pro Ser Leu Pro Pro Pro Glu Lys Met Ser Glu
    170                 175                 180

GCC TAT TCT GCA AAG ATT GCT CTT TTT GGT GCT GGG CCT GCA AGT ATA        687
Ala Tyr Ser Ala Lys Ile Ala Leu Phe Gly Ala Gly Pro Ala Ser Ile
185                 190                 195                 200

AGT TGT GCT TCC TTT TTG GCT CGA TTG GGG TAC TCT GAC ATC ACT ATA        735
Ser Cys Ala Ser Phe Leu Ala Arg Leu Gly Tyr Ser Asp Ile Thr Ile
                205                 210                 215

TTT GAA AAA CAA GAA TAT GTT GGT GGT TTA AGT ACT TCT GAA ATT CCT        783
Phe Glu Lys Gln Glu Tyr Val Gly Gly Leu Ser Thr Ser Glu Ile Pro
            220                 225                 230

CAG TTC CGG CTG CCG TAT GAT GTA GTG AAT TTT GAG ATT GAG CTA ATG        831
Gln Phe Arg Leu Pro Tyr Asp Val Val Asn Phe Glu Ile Glu Leu Met
        235                 240                 245

AAG GAC CTT GGT GTA AAG ATA ATT TGC GGT AAA AGC CTT TCA GTG AAT        879
Lys Asp Leu Gly Val Lys Ile Ile Cys Gly Lys Ser Leu Ser Val Asn
```

```
              250                           255                           260
GAA   ATG   ACT   CTT   AGC   ACT   TTG   AAA   GAA   AAA   GGC   TAC   AAA   GCT   GCT   TTC         927
Glu   Met   Thr   Leu   Ser   Thr   Leu   Lys   Glu   Lys   Gly   Tyr   Lys   Ala   Ala   Phe
265               270                           275                           280

ATT   GGA   ATA   GGT   TTG   CCA   GAA   CCC   AAT   AAA   GAT   GCC   ATC   TTC   CAA   GGC         975
Ile   Gly   Ile   Gly   Leu   Pro   Glu   Pro   Asn   Lys   Asp   Ala   Ile   Phe   Gln   Gly
                        285                           290                           295

CTG   ACG   CAG   GAC   CAG   GGG   TTT   TAT   ACA   TCC   AAA   GAC   TTT   TTG   CCA   CTT        1023
Leu   Thr   Gln   Asp   Gln   Gly   Phe   Tyr   Thr   Ser   Lys   Asp   Phe   Leu   Pro   Leu
                        300                           305                           310

GTA   GCC   AAA   GGC   AGT   AAA   GCA   GGA   ATG   TGC   GCC   TGT   CAC   TCT   CCA   TTG        1071
Val   Ala   Lys   Gly   Ser   Lys   Ala   Gly   Met   Cys   Ala   Cys   His   Ser   Pro   Leu
                  315                           320                           325

CCA   TCG   ATA   CGG   GGA   GTC   GTG   ATT   GTA   CTT   GGA   GCT   GGA   GAC   ACT   GCC        1119
Pro   Ser   Ile   Arg   Gly   Val   Val   Ile   Val   Leu   Gly   Ala   Gly   Asp   Thr   Ala
330                           335                           340

TTC   GAC   TGT   GCA   ACA   TCT   GCT   CTA   CGT   TGT   GGA   GCT   CGC   CGA   GTG   TTC        1167
Phe   Asp   Cys   Ala   Thr   Ser   Ala   Leu   Arg   Cys   Gly   Ala   Arg   Arg   Val   Phe
345                           350                           355                           360

ATC   GTC   TTC   AGA   AAA   GGC   TTT   GTT   AAT   ATA   AGA   GCT   GTC   CCT   GAG   GAG        1215
Ile   Val   Phe   Arg   Lys   Gly   Phe   Val   Asn   Ile   Arg   Ala   Val   Pro   Glu   Glu
                        365                           370                           375

ATG   GAG   CTT   GCT   AAG   GAA   GAA   AAG   TGT   GAA   TTT   CTG   CCA   TTC   CTG   TCC        1263
Met   Glu   Leu   Ala   Lys   Glu   Glu   Lys   Cys   Glu   Phe   Leu   Pro   Phe   Leu   Ser
                  380                           385                           390

CCA   CGG   AAG   GTT   ATA   GTA   AAA   GGT   GGG   AGA   ATT   GTT   GCT   ATG   CAG   TTT        1311
Pro   Arg   Lys   Val   Ile   Val   Lys   Gly   Gly   Arg   Ile   Val   Ala   Met   Gln   Phe
            395                           400                           405

GTT   CGG   ACA   GAG   CAA   GAT   GAA   ACT   GGA   AAA   TGG   AAT   GAA   GAT   GAA   GAT        1359
Val   Arg   Thr   Glu   Gln   Asp   Glu   Thr   Gly   Lys   Trp   Asn   Glu   Asp   Glu   Asp
      410                           415                           420

CAG   ATG   GTC   CAT   CTG   AAA   GCC   GAT   GTG   GTC   ATC   AGT   GCC   TTT   GGT   TCA        1407
Gln   Met   Val   His   Leu   Lys   Ala   Asp   Val   Val   Ile   Ser   Ala   Phe   Gly   Ser
425                           430                           435                           440

GTT   CTG   AGT   GAT   CCT   AAA   GTA   AAA   GAA   GCC   TTG   AGC   CCT   ATA   AAA   TTT        1455
Val   Leu   Ser   Asp   Pro   Lys   Val   Lys   Glu   Ala   Leu   Ser   Pro   Ile   Lys   Phe
                        445                           450                           455

AAC   AGA   TGG   GGT   CTC   CCA   GAA   GTA   GAT   CCA   GAA   ACT   ATG   CAA   ACT   AGT        1503
Asn   Arg   Trp   Gly   Leu   Pro   Glu   Val   Asp   Pro   Glu   Thr   Met   Gln   Thr   Ser
                  460                           465                           470

GAA   GCA   TGG   GTA   TTT   GCA   GGT   GGT   GAT   GTC   GTT   GGT   TTG   GCT   AAC   ACT        1551
Glu   Ala   Trp   Val   Phe   Ala   Gly   Gly   Asp   Val   Val   Gly   Leu   Ala   Asn   Thr
            475                           480                           485

ACA   GTG   GAA   TCG   GTG   AAT   GAT   GGA   AAG   CAA   GCT   TCT   TGG   TAC   ATT   CAC        1599
Thr   Val   Glu   Ser   Val   Asn   Asp   Gly   Lys   Gln   Ala   Ser   Trp   Tyr   Ile   His
      490                           495                           500

AAA   TAC   GTA   CAG   TCA   CAA   TAT   GGA   GCT   TCC   GTT   TCT   GCC   AAG   CCT   GAA        1647
Lys   Tyr   Val   Gln   Ser   Gln   Tyr   Gly   Ala   Ser   Val   Ser   Ala   Lys   Pro   Glu
505                           510                           515                           520

CTA   CCC   CTC   TTT   TAC   ACT   CCT   ATT   GAT   CTG   GTG   GAC   ATT   AGT   GTA   GAA        1695
Leu   Pro   Leu   Phe   Tyr   Thr   Pro   Ile   Asp   Leu   Val   Asp   Ile   Ser   Val   Glu
                        525                           530                           535

ATG   GCC   GGA   TTG   AAG   TTT   ATA   AAT   CCT   TTT   GGT   CTT   GCT   AGC   GCA   ACT        1743
Met   Ala   Gly   Leu   Lys   Phe   Ile   Asn   Pro   Phe   Gly   Leu   Ala   Ser   Ala   Thr
                  540                           545                           550

CCA   GCC   ACC   AGC   ACA   TCA   ATG   ATT   CGA   AGA   GCT   TTT   GAA   GCT   GGA   TGG        1791
Pro   Ala   Thr   Ser   Thr   Ser   Met   Ile   Arg   Arg   Ala   Phe   Glu   Ala   Gly   Trp
            555                           560                           565

GGT   TTT   GCC   CTC   ACC   AAA   ACT   TTC   TCT   CTT   GAT   AAG   GAC   ATT   GTG   ACA        1839
Gly   Phe   Ala   Leu   Thr   Lys   Thr   Phe   Ser   Leu   Asp   Lys   Asp   Ile   Val   Thr
```

-continued

|     |     |     |     |     | 570 |     |     |     |     | 575 |     |     |     |     | 580 |     |      |
|-----|-----|-----|-----|-----|-----|-----|-----|-----|-----|-----|-----|-----|-----|-----|-----|-----|------|
| AAT | GTT | TCC | CCC | AGA | ATC | ATC | CGG | GGA | ACC | ACC | TCT | GGC | CCC | ATG | TAT |     | 1887 |
| Asn | Val | Ser | Pro | Arg | Ile | Ile | Arg | Gly | Thr | Thr | Ser | Gly | Pro | Met | Tyr |     |      |
| 585 |     |     |     |     | 590 |     |     |     |     | 595 |     |     |     |     | 600 |     |      |

| GGC | CCT | GGA | CAA | AGC | TCC | TTT | CTG | AAT | ATT | GAG | CTC | ATC | AGT | GAG | AAA |     | 1935 |
|-----|-----|-----|-----|-----|-----|-----|-----|-----|-----|-----|-----|-----|-----|-----|-----|-----|------|
| Gly | Pro | Gly | Gln | Ser | Ser | Phe | Leu | Asn | Ile | Glu | Leu | Ile | Ser | Glu | Lys |     |      |
|     |     |     |     |     | 605 |     |     |     |     | 610 |     |     |     |     | 615 |     |      |

| ACG | GCT | GCA | TAT | TGG | TGT | CAA | AGT | GTC | ACT | GAA | CTA | AAG | GCT | GAC | TTC |     | 1983 |
| Thr | Ala | Ala | Tyr | Trp | Cys | Gln | Ser | Val | Thr | Glu | Leu | Lys | Ala | Asp | Phe |     |      |
|     |     |     | 620 |     |     |     |     | 625 |     |     |     |     | 630 |     |     |     |      |

| CCA | GAC | AAC | ATT | GTG | ATT | GCT | AGC | ATT | ATG | TGC | AGT | TAC | AAT | AAA | AAT |     | 2031 |
| Pro | Asp | Asn | Ile | Val | Ile | Ala | Ser | Ile | Met | Cys | Ser | Tyr | Asn | Lys | Asn |     |      |
|     |     | 635 |     |     |     |     | 640 |     |     |     |     | 645 |     |     |     |     |      |

| GAC | TGG | ACG | GAA | CTT | GCC | AAG | AAG | TCT | GAG | GAT | TCT | GGA | GCA | GAT | GCC |     | 2079 |
| Asp | Trp | Thr | Glu | Leu | Ala | Lys | Lys | Ser | Glu | Asp | Ser | Gly | Ala | Asp | Ala |     |      |
| 650 |     |     |     |     | 655 |     |     |     |     | 660 |     |     |     |     |     |     |      |

| CTG | GAG | TTA | AAT | TTA | TCA | TGT | CCA | CAT | GGC | ATG | GGA | GAA | AGA | GGA | ATG |     | 2127 |
| Leu | Glu | Leu | Asn | Leu | Ser | Cys | Pro | His | Gly | Met | Gly | Glu | Arg | Gly | Met |     |      |
| 665 |     |     |     |     | 670 |     |     |     |     | 675 |     |     |     |     | 680 |     |      |

| GGC | CTG | GCC | TGT | GGG | CAG | GAT | CCA | GAG | CTG | GTG | CGG | AAC | ATC | TGC | CGC |     | 2175 |
| Gly | Leu | Ala | Cys | Gly | Gln | Asp | Pro | Glu | Leu | Val | Arg | Asn | Ile | Cys | Arg |     |      |
|     |     |     |     | 685 |     |     |     |     | 690 |     |     |     |     | 695 |     |     |      |

| TGG | GTT | AGG | CAA | GCT | GTT | CAG | ATT | CCT | TTT | TTT | GCC | AAG | CTG | ACC | CCA |     | 2223 |
| Trp | Val | Arg | Gln | Ala | Val | Gln | Ile | Pro | Phe | Phe | Ala | Lys | Leu | Thr | Pro |     |      |
|     |     |     | 700 |     |     |     |     | 705 |     |     |     |     | 710 |     |     |     |      |

| AAT | GTC | ACT | GAT | ATT | GTG | AGC | ATC | GCA | AGA | GCT | GCA | AAG | GAA | GGT | GGT |     | 2271 |
| Asn | Val | Thr | Asp | Ile | Val | Ser | Ile | Ala | Arg | Ala | Ala | Lys | Glu | Gly | Gly |     |      |
|     |     | 715 |     |     |     |     | 720 |     |     |     |     | 725 |     |     |     |     |      |

| GCC | AAT | GGC | GTT | ACA | GCC | ACC | AAC | ACT | GTC | TCA | GGT | CTG | ATG | GGA | TTA |     | 2319 |
| Ala | Asn | Gly | Val | Thr | Ala | Thr | Asn | Thr | Val | Ser | Gly | Leu | Met | Gly | Leu |     |      |
|     | 730 |     |     |     |     | 735 |     |     |     |     | 740 |     |     |     |     |     |      |

| AAA | TCT | GAT | GGC | ACA | CCT | TGG | CCA | GCA | GTG | GGG | ATT | GCA | AAG | CGA | ACT |     | 2367 |
| Lys | Ser | Asp | Gly | Thr | Pro | Trp | Pro | Ala | Val | Gly | Ile | Ala | Lys | Arg | Thr |     |      |
| 745 |     |     |     |     | 750 |     |     |     |     | 755 |     |     |     |     | 760 |     |      |

| ACA | TAT | GGA | GGA | GTG | TCT | GGG | ACA | GCA | ATC | AGA | CCT | ATT | GCT | TTG | AGA |     | 2415 |
| Thr | Tyr | Gly | Gly | Val | Ser | Gly | Thr | Ala | Ile | Arg | Pro | Ile | Ala | Leu | Arg |     |      |
|     |     |     |     | 765 |     |     |     |     | 770 |     |     |     |     | 775 |     |     |      |

| GCT | GTG | ACC | TCC | ATT | GCT | CGT | GCT | CTG | CCT | GGA | TTT | CCC | ATT | TTG | GCT |     | 2463 |
| Ala | Val | Thr | Ser | Ile | Ala | Arg | Ala | Leu | Pro | Gly | Phe | Pro | Ile | Leu | Ala |     |      |
|     |     |     | 780 |     |     |     |     | 785 |     |     |     |     | 790 |     |     |     |      |

| ACT | GGT | GGA | ATT | GAC | TCT | GCT | GAA | AGT | GGT | CTT | CAG | TTT | CTC | CAT | AGT |     | 2511 |
| Thr | Gly | Gly | Ile | Asp | Ser | Ala | Glu | Ser | Gly | Leu | Gln | Phe | Leu | His | Ser |     |      |
|     |     | 795 |     |     |     |     | 800 |     |     |     |     | 805 |     |     |     |     |      |

| GGT | GCT | TCC | GTC | CTC | CAG | GTA | TGC | AGT | GCC | ATT | CAG | AAT | CAG | GAT | TTC |     | 2559 |
| Gly | Ala | Ser | Val | Leu | Gln | Val | Cys | Ser | Ala | Ile | Gln | Asn | Gln | Asp | Phe |     |      |
| 810 |     |     |     |     | 815 |     |     |     |     | 820 |     |     |     |     |     |     |      |

| ACT | GTG | ATC | GAA | GAC | TAC | TGC | ACT | GGC | CTC | AAA | GCC | CTG | CTT | TAT | CTG |     | 2607 |
| Thr | Val | Ile | Glu | Asp | Tyr | Cys | Thr | Gly | Leu | Lys | Ala | Leu | Leu | Tyr | Leu |     |      |
| 825 |     |     |     |     | 830 |     |     |     |     | 835 |     |     |     |     | 840 |     |      |

| AAA | AGC | ATT | GAA | GAA | CTA | CAA | GAC | TGG | GAT | GGA | CAG | AGT | CCA | GCT | ACT |     | 2655 |
| Lys | Ser | Ile | Glu | Glu | Leu | Gln | Asp | Trp | Asp | Gly | Gln | Ser | Pro | Ala | Thr |     |      |
|     |     |     |     | 845 |     |     |     |     | 850 |     |     |     |     | 855 |     |     |      |

| GTG | AGT | CAC | CAG | AAA | GGG | AAA | CCA | GTT | CCA | CGT | ATA | GCT | GAA | CTC | ATG |     | 2703 |
| Val | Ser | His | Gln | Lys | Gly | Lys | Pro | Val | Pro | Arg | Ile | Ala | Glu | Leu | Met |     |      |
|     |     |     | 860 |     |     |     |     | 865 |     |     |     |     | 870 |     |     |     |      |

| GAC | AAG | AAA | CTG | CCA | AGT | TTT | GGA | CCT | TAT | CTG | GAA | CAG | CGC | AAG | AAA |     | 2751 |
| Asp | Lys | Lys | Leu | Pro | Ser | Phe | Gly | Pro | Tyr | Leu | Glu | Gln | Arg | Lys | Lys |     |      |
|     |     | 875 |     |     |     |     | 880 |     |     |     |     | 885 |     |     |     |     |      |

| ATC | ATA | GCA | GAA | AAC | AAG | ATT | AGA | CTG | AAA | GAA | CAA | AAT | GTA | GCT | TTT |     | 2799 |
| Ile | Ile | Ala | Glu | Asn | Lys | Ile | Arg | Leu | Lys | Glu | Gln | Asn | Val | Ala | Phe |     |      |

-continued

|     |     |     | 890 |     |     |     |     | 895 |     |     |     |     | 900 |     |     |      |
|-----|-----|-----|-----|-----|-----|-----|-----|-----|-----|-----|-----|-----|-----|-----|-----|------|
| TCA | CCA | CTT | AAG | AGA | AGC | TGT | TTT | ATC | CCC | AAA | AGG | CCT | ATT | CCT | ACC | 2847 |
| Ser | Pro | Leu | Lys | Arg | Ser | Cys | Phe | Ile | Pro | Lys | Arg | Pro | Ile | Pro | Thr |      |
| 905 |     |     |     |     | 910 |     |     |     |     | 915 |     |     |     |     | 920 |      |
| ATC | AAG | GAT | GTA | ATA | GGA | AAA | GCA | CTG | CAG | TAC | CTT | GGA | ACA | TTT | GGT | 2895 |
| Ile | Lys | Asp | Val | Ile | Gly | Lys | Ala | Leu | Gln | Tyr | Leu | Gly | Thr | Phe | Gly |      |
|     |     |     |     | 925 |     |     |     |     | 930 |     |     |     |     | 935 |     |      |
| GAA | TTG | AGC | AAC | GTA | GAG | CAA | GTT | GTG | GCT | ATG | ATT | GAT | GAA | GAA | ATG | 2943 |
| Glu | Leu | Ser | Asn | Val | Glu | Gln | Val | Val | Ala | Met | Ile | Asp | Glu | Glu | Met |      |
|     |     |     | 940 |     |     |     |     | 945 |     |     |     |     | 950 |     |     |      |
| TGT | ATC | AAC | TGT | GGT | AAA | TGC | TAC | ATG | ACC | TGT | AAT | GAT | TCT | GGC | TAC | 2991 |
| Cys | Ile | Asn | Cys | Gly | Lys | Cys | Tyr | Met | Thr | Cys | Asn | Asp | Ser | Gly | Tyr |      |
|     |     | 955 |     |     |     |     | 960 |     |     |     |     | 965 |     |     |     |      |
| CAG | GCT | ATA | CAG | TTT | GAT | CCA | GAA | ACC | CAC | CTG | CCC | ACC | ATA | ACC | GAC | 3039 |
| Gln | Ala | Ile | Gln | Phe | Asp | Pro | Glu | Thr | His | Leu | Pro | Thr | Ile | Thr | Asp |      |
|     | 970 |     |     |     |     | 975 |     |     |     |     | 980 |     |     |     |     |      |
| ACT | TGT | ACA | GGC | TGT | ACT | CTG | TGT | CTC | AGT | GTT | TGC | CCT | ATT | GTC | GAC | 3087 |
| Thr | Cys | Thr | Gly | Cys | Thr | Leu | Cys | Leu | Ser | Val | Cys | Pro | Ile | Val | Asp |      |
| 985 |     |     |     |     | 990 |     |     |     |     | 995 |     |     |     |     | 1000|      |
| TGC | ATC | AAA | ATG | GTT | TCC | AGG | ACA | ACA | CCT | TAT | GAA | CCA | AAG | AGA | GGC | 3135 |
| Cys | Ile | Lys | Met | Val | Ser | Arg | Thr | Thr | Pro | Tyr | Glu | Pro | Lys | Arg | Gly |      |
|     |     |     |     | 1005|     |     |     |     | 1010|     |     |     |     | 1015|     |      |
| GTA | CCC | TTA | TCT | GTG | AAT | CCG | GTG | TGT | TAAGGTGATT | | TGTGAAACAG | | | | | 3182 |
| Val | Pro | Leu | Ser | Val | Asn | Pro | Val | Cys |     |     |     |     |     |     |     |      |
|     |     |     |     | 1020|     |     |     | 1025|     |     |     |     |     |     |     |      |

| TTGCTGTGAA | CTTTCATGTC | ACCTACATAT | GCTGATCTCT | TAAAATCATG | ATCCTTGTGT | 3242 |
| TCAGCTCTTT | CCAAATTAAA | ACAAATATAC | ATTTTCTAAA | TAAAAATATG | TAATTTCAAA | 3302 |
| ATACATTTGT | AAGTGTAAAA | AATGTCTCAT | GTCAATGACC | ATTCAATTAG | TGGCATAAAA | 3362 |
| TAGAATAATT | CTTTTCTGAG | GATAGTAGTT | AAATAACTGT | GTGGCAGTTA | ATTGGATGTT | 3422 |
| CACTGCCAGT | TGTCTTATGT | GAAAAATTAA | CTTTTGTGT  | GGCAATTAGT | GTGACAGTTT | 3482 |
| CCAAATTGCC | CTATGCTGTG | CTCCATATTT | GATTTCTAAT | TGTAAGTGAA | ATTAAGCATT | 3542 |
| TTGAAACAAA | GTACTCTTTA | ACATACAAGA | AAATGTATCC | AAGGAAACAT | TTTATCAATA | 3602 |
| AAAATTACCT | TTAATTTTAA | TGCTGTTTCT | AAGAAAATGT | AGTTAGCTCC | ATAAAGTACA | 3662 |
| AATGAAGAAA | GTCAAAAATT | ATTTGCTATG | GCAGGATAAG | AAAGCCTAAA | ATTGAGTTTG | 3722 |
| TGGACTTTAT | TAAGTAAAAT | CCCCTTCGCT | GAAATTGCTT | ATTTTGGTG  | TTGGATAGAG | 3782 |
| GATAGGGAGA | ATATTTACTA | ACTAAATACC | ATTCACTACT | CATGCGTGAG | ATGGGTGTAC | 3842 |
| AAACTCATCC | TCTTTTAATG | GCATTTCTCT | TTAAACTATG | TTCCTAACCA | AATGAGATGA | 3902 |
| TAGGATAGAT | CCTGGTTACC | ACTCTTTTAC | TGTGCACATA | TGGGCCCCGG | AATTC      | 3957 |

( 2 ) INFORMATION FOR SEQ ID NO:2:

( i ) SEQUENCE CHARACTERISTICS:
        ( A ) LENGTH: 1025 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Pro | Val | Leu | Ser | Lys | Asp | Ser | Ala | Asp | Ile | Glu | Ser | Ile | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Leu | Asn | Pro | Arg | Thr | Gln | Thr | His | Ala | Thr | Leu | Cys | Ser | Thr | Ser |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Lys | Lys | Leu | Asp | Lys | Lys | His | Trp | Lys | Arg | Asn | Pro | Asp | Lys | Asn |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

```
Cys Phe Asn Cys Glu Lys Leu Glu Asn Asn Phe Asp Asp Ile Lys His
         50                  55                  60

Thr Thr Leu Gly Glu Arg Gly Ala Leu Arg Glu Ala Met Arg Cys Leu
 65                  70                  75                  80

Lys Cys Ala Asp Ala Pro Cys Gln Lys Ser Cys Pro Thr Asn Leu Asp
                 85                  90                      95

Ile Lys Ser Phe Ile Thr Ser Ile Ala Asn Lys Asn Tyr Tyr Gly Ala
            100                 105                 110

Ala Lys Met Ile Phe Ser Asp Asn Pro Leu Gly Leu Thr Cys Gly Met
            115                 120                 125

Val Cys Pro Thr Ser Asp Leu Cys Val Gly Gly Cys Asn Leu Tyr Ala
    130                 135                 140

Thr Glu Glu Gly Pro Ile Asn Ile Gly Gly Leu Gln Gln Phe Ala Thr
145                 150                 155                 160

Glu Val Phe Lys Ala Met Ser Ile Pro Gln Ile Arg Asn Pro Ser Leu
                165                 170                 175

Pro Pro Pro Glu Lys Met Ser Glu Ala Tyr Ser Ala Lys Ile Ala Leu
            180                 185                 190

Phe Gly Ala Gly Pro Ala Ser Ile Ser Cys Ala Ser Phe Leu Ala Arg
            195                 200                 205

Leu Gly Tyr Ser Asp Ile Thr Ile Phe Glu Lys Glu Tyr Val Gly
    210                 215                 220

Gly Leu Ser Thr Ser Glu Ile Pro Gln Phe Arg Leu Pro Tyr Asp Val
225                 230                 235                 240

Val Asn Phe Glu Ile Glu Leu Met Lys Asp Leu Gly Val Lys Ile Ile
                245                 250                 255

Cys Gly Lys Ser Leu Ser Val Asn Glu Met Thr Leu Ser Thr Leu Lys
            260                 265                 270

Glu Lys Gly Tyr Lys Ala Ala Phe Ile Gly Ile Gly Leu Pro Glu Pro
        275                 280                 285

Asn Lys Asp Ala Ile Phe Gln Gly Leu Thr Gln Asp Gln Gly Phe Tyr
    290                 295                 300

Thr Ser Lys Asp Phe Leu Pro Leu Val Ala Lys Gly Ser Lys Ala Gly
305                 310                 315                 320

Met Cys Ala Cys His Ser Pro Leu Pro Ser Ile Arg Gly Val Val Ile
                325                 330                 335

Val Leu Gly Ala Gly Asp Thr Ala Phe Asp Cys Ala Thr Ser Ala Leu
            340                 345                 350

Arg Cys Gly Ala Arg Arg Val Phe Ile Val Phe Arg Lys Gly Phe Val
    355                 360                 365

Asn Ile Arg Ala Val Pro Glu Glu Met Glu Leu Ala Lys Glu Glu Lys
370                 375                 380

Cys Glu Phe Leu Pro Phe Leu Ser Pro Arg Lys Val Ile Val Lys Gly
385                 390                 395                 400

Gly Arg Ile Val Ala Met Gln Phe Val Arg Thr Glu Gln Asp Glu Thr
                405                 410                 415

Gly Lys Trp Asn Glu Asp Glu Asp Gln Met Val His Leu Lys Ala Asp
            420                 425                 430

Val Val Ile Ser Ala Phe Gly Ser Val Leu Ser Asp Pro Lys Val Lys
            435                 440                 445

Glu Ala Leu Ser Pro Ile Lys Phe Asn Arg Trp Gly Leu Pro Glu Val
450                 455                 460

Asp Pro Glu Thr Met Gln Thr Ser Glu Ala Trp Val Phe Ala Gly Gly
```

-continued

```
465                     470                     475                     480
Asp  Val  Val  Gly  Leu  Ala  Asn  Thr  Thr  Val  Glu  Ser  Val  Asn  Asp  Gly
                    485                     490                     495
Lys  Gln  Ala  Ser  Trp  Tyr  Ile  His  Lys  Tyr  Val  Gln  Ser  Gln  Tyr  Gly
               500                     505                     510
Ala  Ser  Val  Ser  Ala  Lys  Pro  Glu  Leu  Pro  Leu  Phe  Tyr  Thr  Pro  Ile
               515                     520                     525
Asp  Leu  Val  Asp  Ile  Ser  Val  Glu  Met  Ala  Gly  Leu  Lys  Phe  Ile  Asn
     530                     535                     540
Pro  Phe  Gly  Leu  Ala  Ser  Ala  Thr  Pro  Ala  Thr  Ser  Thr  Ser  Met  Ile
545                     550                     555                     560
Arg  Arg  Ala  Phe  Glu  Ala  Gly  Trp  Gly  Phe  Ala  Leu  Thr  Lys  Thr  Phe
                    565                     570                     575
Ser  Leu  Asp  Lys  Asp  Ile  Val  Thr  Asn  Val  Ser  Pro  Arg  Ile  Ile  Arg
               580                     585                     590
Gly  Thr  Thr  Ser  Gly  Pro  Met  Tyr  Gly  Pro  Gly  Gln  Ser  Ser  Phe  Leu
          595                     600                     605
Asn  Ile  Glu  Leu  Ile  Ser  Glu  Lys  Thr  Ala  Ala  Tyr  Trp  Cys  Gln  Ser
     610                     615                     620
Val  Thr  Glu  Leu  Lys  Ala  Asp  Phe  Pro  Asp  Asn  Ile  Val  Ile  Ala  Ser
625                     630                     635                     640
Ile  Met  Cys  Ser  Tyr  Asn  Lys  Asn  Asp  Trp  Thr  Glu  Leu  Ala  Lys  Lys
                    645                     650                     655
Ser  Glu  Asp  Ser  Gly  Ala  Asp  Ala  Leu  Glu  Leu  Asn  Leu  Ser  Cys  Pro
               660                     665                     670
His  Gly  Met  Gly  Glu  Arg  Gly  Met  Gly  Leu  Ala  Cys  Gly  Gln  Asp  Pro
          675                     680                     685
Glu  Leu  Val  Arg  Asn  Ile  Cys  Arg  Trp  Val  Arg  Gln  Ala  Val  Gln  Ile
     690                     695                     700
Pro  Phe  Phe  Ala  Lys  Leu  Thr  Pro  Asn  Val  Thr  Asp  Ile  Val  Ser  Ile
705                     710                     715                     720
Ala  Arg  Ala  Ala  Lys  Glu  Gly  Gly  Ala  Asn  Gly  Val  Thr  Ala  Thr  Asn
                    725                     730                     735
Thr  Val  Ser  Gly  Leu  Met  Gly  Leu  Lys  Ser  Asp  Gly  Thr  Pro  Trp  Pro
               740                     745                     750
Ala  Val  Gly  Ile  Ala  Lys  Arg  Thr  Thr  Tyr  Gly  Gly  Val  Ser  Gly  Thr
          755                     760                     765
Ala  Ile  Arg  Pro  Ile  Ala  Leu  Arg  Ala  Val  Thr  Ser  Ile  Ala  Arg  Ala
     770                     775                     780
Leu  Pro  Gly  Phe  Pro  Ile  Leu  Ala  Thr  Gly  Gly  Ile  Asp  Ser  Ala  Glu
785                     790                     795                     800
Ser  Gly  Leu  Gln  Phe  Leu  His  Ser  Gly  Ala  Ser  Val  Leu  Gln  Val  Cys
                    805                     810                     815
Ser  Ala  Ile  Gln  Asn  Gln  Asp  Phe  Thr  Val  Ile  Glu  Asp  Tyr  Cys  Thr
               820                     825                     830
Gly  Leu  Lys  Ala  Leu  Leu  Tyr  Leu  Lys  Ser  Ile  Glu  Glu  Leu  Gln  Asp
          835                     840                     845
Trp  Asp  Gly  Gln  Ser  Pro  Ala  Thr  Val  Ser  His  Gln  Lys  Gly  Lys  Pro
     850                     855                     860
Val  Pro  Arg  Ile  Ala  Glu  Leu  Met  Asp  Lys  Lys  Leu  Pro  Ser  Phe  Gly
865                     870                     875                     880
Pro  Tyr  Leu  Glu  Gln  Arg  Lys  Lys  Ile  Ile  Ala  Glu  Asn  Lys  Ile  Arg
                    885                     890                     895
```

-continued

| | | | | | | | | | | | | | | |
|---|---|---|---|---|---|---|---|---|---|---|---|---|---|---|
| Leu | Lys | Glu | Gln | Asn | Val | Ala | Phe | Ser | Pro | Leu | Lys | Arg | Ser | Cys | Phe |
| | | | 900 | | | | 905 | | | | | 910 | | |
| Ile | Pro | Lys | Arg | Pro | Ile | Pro | Thr | Ile | Lys | Asp | Val | Ile | Gly | Lys | Ala |
| | | 915 | | | | 920 | | | | | 925 | | | |
| Leu | Gln | Tyr | Leu | Gly | Thr | Phe | Gly | Glu | Leu | Ser | Asn | Val | Glu | Gln | Val |
| | 930 | | | | | 935 | | | | | 940 | | | |
| Val | Ala | Met | Ile | Asp | Glu | Met | Cys | Ile | Asn | Cys | Gly | Lys | Cys | Tyr |
| 945 | | | | 950 | | | | | 955 | | | | | 960 |
| Met | Thr | Cys | Asn | Asp | Ser | Gly | Tyr | Gln | Ala | Ile | Gln | Phe | Asp | Pro | Glu |
| | | | 965 | | | | | 970 | | | | | 975 | |
| Thr | His | Leu | Pro | Thr | Ile | Thr | Asp | Thr | Cys | Thr | Gly | Cys | Thr | Leu | Cys |
| | | | 980 | | | | 985 | | | | | 990 | | |
| Leu | Ser | Val | Cys | Pro | Ile | Val | Asp | Cys | Ile | Lys | Met | Val | Ser | Arg | Thr |
| | | 995 | | | | 1000 | | | | | 1005 | | | |
| Thr | Pro | Tyr | Glu | Pro | Lys | Arg | Gly | Val | Pro | Leu | Ser | Val | Asn | Pro | Val |
| | 1010 | | | | | 1015 | | | | | 1020 | | | |
| Cys | | | | | | | | | | | | | | |
| 1025 | | | | | | | | | | | | | | |

(2) INFORMATION FOR SEQ ID NO:3:

(i) SEQUENCE CHARACTERISTICS:
        (A) LENGTH: 4447 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 88..3162

(ix) FEATURE:
        (A) NAME/KEY: misc_feature
        (B) LOCATION: 1..4447
        (D) OTHER INFORMATION: /product= "Pig DPD"

(xi) SEQUENCE DESCRIPTION: SEQ ID NO:3:

| | | | | | | | | | |
|---|---|---|---|---|---|---|---|---|---|
| GGACACTCGA | CCCACGCGTC | CGCCGGCCGG | AGGCGGAGGA | CGCGGGGAGG | GCCCGCCGGT | | | | 60 |
| GGGAGACTCC | AAGCTGTCGG | CATCGCC ATG | GCC CCT GTG | CTG AGC AAG | GAC | | | | 111 |
| | | Met | Ala Pro Val | Leu Ser Lys | Asp | | | | |
| | | 1 | | 5 | | | | | |

| | | | | | | | | | | |
|---|---|---|---|---|---|---|---|---|---|---|
| GTG | GCG | GAC | ATC | GAG | AGT | ATC | CTG | GCT | TTA | AAT | CCT | CGA | ACA | CAG | TCT | 159 |
| Val | Ala | Asp | Ile | Glu | Ser | Ile | Leu | Ala | Leu | Asn | Pro | Arg | Thr | Gln | Ser | |
| | 10 | | | | 15 | | | | | 20 | | | | | | |
| CAT | GCA | GCC | CTT | CAT | TCC | ACT | TTG | GCC | AAG | AAA | TTG | GAT | AAG | AAA | CAC | 207 |
| His | Ala | Ala | Leu | His | Ser | Thr | Leu | Ala | Lys | Lys | Leu | Asp | Lys | Lys | His | |
| 25 | | | | | 30 | | | | | 35 | | | | | 40 | |
| TGG | AAA | AGA | AAT | CCC | GAT | AAG | AAC | TGC | TTT | CAT | TGC | GAG | AAG | CTG | GAG | 255 |
| Trp | Lys | Arg | Asn | Pro | Asp | Lys | Asn | Cys | Phe | His | Cys | Glu | Lys | Leu | Glu | |
| | | | | 45 | | | | | 50 | | | | | 55 | | |
| AAT | AAT | TTT | GGT | GAC | ATC | AAG | CAC | ACG | ACT | CTT | GGT | GAG | CGA | GGA | GCT | 303 |
| Asn | Asn | Phe | Gly | Asp | Ile | Lys | His | Thr | Thr | Leu | Gly | Glu | Arg | Gly | Ala | |
| | | | 60 | | | | | 65 | | | | | 70 | | | |
| CTC | CGA | GAA | GCA | ATG | AGA | TGC | CTG | AAA | TGT | GCC | GAT | GCT | CCC | TGT | CAG | 351 |
| Leu | Arg | Glu | Ala | Met | Arg | Cys | Leu | Lys | Cys | Ala | Asp | Ala | Pro | Cys | Gln | |
| | | 75 | | | | | 80 | | | | | 85 | | | | |
| AAG | AGC | TGT | CCA | ACT | CAT | CTA | GAT | ATC | AAA | TCA | TTC | ATC | ACA | AGT | ATC | 399 |
| Lys | Ser | Cys | Pro | Thr | His | Leu | Asp | Ile | Lys | Ser | Phe | Ile | Thr | Ser | Ile | |
| | 90 | | | | | 95 | | | | | 100 | | | | | |
| TCA | AAT | AAG | AAC | TAT | TAT | GGA | GCT | GCT | AAG | ATG | ATT | TTT | TCT | GAC | AAC | 447 |

```
Ser Asn Lys Asn Tyr Tyr Gly Ala Ala Lys Met Ile Phe Ser Asp Asn
105                 110                 115                 120

CCT CTT GGT CTG ACC TGT GGA ATG GTA TGT CCA ACC TCT GAT CTT TGT      495
Pro Leu Gly Leu Thr Cys Gly Met Val Cys Pro Thr Ser Asp Leu Cys
                125                 130                 135

GTA GGA GGA TGC AAT TTA TAT GCA ACT GAA GAG GGA TCA ATT AAT ATT      543
Val Gly Gly Cys Asn Leu Tyr Ala Thr Glu Glu Gly Ser Ile Asn Ile
                140                 145                 150

GGT GGA TTG CAG CAG TTT GCT TCT GAG GTG TTC AAA GCA ATG AAT ATC      591
Gly Gly Leu Gln Gln Phe Ala Ser Glu Val Phe Lys Ala Met Asn Ile
                155                 160                 165

CCA CAA ATC AGG AAT CCT TGT CTG CCA TCC CAA GAG AAA ATG CCT GAA      639
Pro Gln Ile Arg Asn Pro Cys Leu Pro Ser Gln Glu Lys Met Pro Glu
                170                 175                 180

GCT TAT TCT GCA AAG ATT GCT CTT TTG GGT GCT GGG CCT GCA AGT ATA      687
Ala Tyr Ser Ala Lys Ile Ala Leu Leu Gly Ala Gly Pro Ala Ser Ile
185                 190                 195                 200

AGC TGT GCT TCC TTC TTG GCT CGA TTA GGC TAC TCT GAC ATC ACT ATA      735
Ser Cys Ala Ser Phe Leu Ala Arg Leu Gly Tyr Ser Asp Ile Thr Ile
                205                 210                 215

TTT GAA AAA CAA GAA TAT GTT GGT GGT TTA AGT ACT TCT GAA ATC CCT      783
Phe Glu Lys Gln Glu Tyr Val Gly Gly Leu Ser Thr Ser Glu Ile Pro
                220                 225                 230

CAG TTC CGG CTG CCA TAT GAT GTA GTG AAT TTT GAG ATT GAG CTT ATG      831
Gln Phe Arg Leu Pro Tyr Asp Val Val Asn Phe Glu Ile Glu Leu Met
                235                 240                 245

AAG GAC CTT GGT GTA AAG ATA ATT TGT GGT AAA AGC CTT TCA GAG AAT      879
Lys Asp Leu Gly Val Lys Ile Ile Cys Gly Lys Ser Leu Ser Glu Asn
                250                 255                 260

GAA ATT ACT CTC AAC ACT TTA AAA GAA GAA GGG TAT AAA GCT GCT TTC      927
Glu Ile Thr Leu Asn Thr Leu Lys Glu Glu Gly Tyr Lys Ala Ala Phe
265                 270                 275                 280

ATT GGT ATA GGT TTG CCA GAA CCC AAA ACG GAT GAC ATC TTC CAA GGC      975
Ile Gly Ile Gly Leu Pro Glu Pro Lys Thr Asp Asp Ile Phe Gln Gly
                285                 290                 295

CTG ACA CAG GAC CAG GGG TTT TAC ACA TCC AAA GAC TTT CTG CCC CTT     1023
Leu Thr Gln Asp Gln Gly Phe Tyr Thr Ser Lys Asp Phe Leu Pro Leu
                300                 305                 310

GTA GCC AAA AGC AGT AAA GCA GGA ATG TGT GCC TGT CAC TCT CCA TTG     1071
Val Ala Lys Ser Ser Lys Ala Gly Met Cys Ala Cys His Ser Pro Leu
                315                 320                 325

CCA TCG ATA CGG GGA GCC GTG ATT GTA CTC GGA GCT GGA GAC ACA GCT     1119
Pro Ser Ile Arg Gly Ala Val Ile Val Leu Gly Ala Gly Asp Thr Ala
                330                 335                 340

TTC GAC TGT GCA ACA TCC GCT TTA CGT TGT GGA GCC CGC CGA GTG TTC     1167
Phe Asp Cys Ala Thr Ser Ala Leu Arg Cys Gly Ala Arg Arg Val Phe
345                 350                 355                 360

CTC GTC TTC AGA AAA GGC TTT GTT AAT ATA AGA GCT GTC CCT GAG GAG     1215
Leu Val Phe Arg Lys Gly Phe Val Asn Ile Arg Ala Val Pro Glu Glu
                365                 370                 375

GTG GAG CTT GCT AAG GAA GAA AAA TGT GAA TTT TTG CCT TTC CTG TCC     1263
Val Glu Leu Ala Lys Glu Glu Lys Cys Glu Phe Leu Pro Phe Leu Ser
                380                 385                 390

CCA CGG AAG GTT ATA GTT AAA GGT GGG AGA ATT GTT GCC GTG CAA TTT     1311
Pro Arg Lys Val Ile Val Lys Gly Gly Arg Ile Val Ala Val Gln Phe
                395                 400                 405

GTT CGA ACA GAA CAA GAT GAA ACT GGA AAA TGG AAT GAA GAT GAA GAT     1359
Val Arg Thr Glu Gln Asp Glu Thr Gly Lys Trp Asn Glu Asp Glu Asp
    410                 415                 420

CAG ATA GTC CAT CTG AAG GCT GAT GTG GTC ATC AGT GCC TTT GGC TCA     1407
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Gln 425 | Ile | Val | His | Leu | Lys 430 | Ala | Asp | Val | Val | Ile 435 | Ser | Ala | Phe | Gly | Ser 440 |      |
| GTG Val | CTG Leu | AGG Arg | GAT Asp | CCT Pro 445 | AAA Lys | GTA Val | AAA Lys | GAA Glu | GCC Ala 450 | TTG Leu | AGC Ser | CCT Pro | ATA Ile | AAA Lys 455 | TTT Phe | 1455 |
| AAC Asn | AGA Arg | TGG Trp | GAT Asp 460 | CTC Leu | CCA Pro | GAA Glu | GTA Val | GAT Asp | CCA Pro 465 | GAA Glu | ACT Thr | ATG Met | CAA Gln | ACC Thr 470 | AGT Ser | 1503 |
| GAA Glu | CCA Pro | TGG Trp 475 | GTG Val | TTT Phe | GCA Ala | GGT Gly | GGT Gly | GAT Asp 480 | ATC Ile | GTT Val | GGT Gly | ATG Met | GCT Ala 485 | AAC Asn | ACT Thr | 1551 |
| ACG Thr | GTG Val 490 | GAA Glu | TCC Ser | GTA Val | AAT Asn | GAC Asp 495 | GGA Gly | AAG Lys | CAG Gln | GCC Ala | TCC Ser 500 | TGG Trp | TAC Tyr | ATT Ile | CAC His | 1599 |
| AAA Lys 505 | TAT Tyr | ATC Ile | CAG Gln | GCC Ala | CAA Gln 510 | TAT Tyr | GGA Gly | GCT Ala | TCA Ser | GTT Val 515 | TCT Ser | GCC Ala | AAG Lys | CCC Pro | GAA Glu 520 | 1647 |
| CTG Leu | CCC Pro | CTG Leu | TTT Phe | TAT Tyr 525 | ACG Thr | CCT Pro | GTT Val | GAC Asp | CTG Leu 530 | GTG Val | GAC Asp | ATC Ile | AGC Ser | GTG Val 535 | GAA Glu | 1695 |
| ATG Met | GCT Ala | GGA Gly | TTA Leu 540 | AAG Lys | TTT Phe | ATA Ile | AAT Asn | CCT Pro 545 | TTT Phe | GGT Gly | CTT Leu | GCC Ala | AGT Ser 550 | GCA Ala | GCT Ala | 1743 |
| CCA Pro | ACT Thr | ACC Thr 555 | AGT Ser | TCA Ser | TCG Ser | ATG Met | ATT Ile 560 | CGA Arg | AGA Arg | GCT Ala | TTT Phe | GAA Glu 565 | GCT Ala | GGA Gly | TGG Trp | 1791 |
| GGT Gly | TTT Phe 570 | GCC Ala | CTG Leu | ACC Thr | AAA Lys | ACT Thr 575 | TTC Phe | TCT Ser | CTT Leu | GAT Asp | AAG Lys 580 | GAC Asp | ATA Ile | GTG Val | ACA Thr | 1839 |
| AAT Asn 585 | GTC Val | TCA Ser | CCC Pro | AGA Arg | ATC Ile 590 | GTC Val | CGG Arg | GGG Gly | ACT Thr | ACC Thr 595 | TCT Ser | GGC Gly | CCC Pro | ATG Met | TAC Tyr 600 | 1887 |
| GGC Gly | CCT Pro | GGA Gly | CAA Gln | AGC Ser 605 | TCC Ser | TTC Phe | CTG Leu | AAT Asn | ATT Ile 610 | GAG Glu | CTC Leu | ATC Ile | AGT Ser | GAA Glu 615 | AAA Lys | 1935 |
| ACA Thr | GCT Ala | GCA Ala | TAT Tyr 620 | TGG Trp | TGT Cys | CAA Gln | AGT Ser | GTC Val 625 | ACT Thr | GAA Glu | CTA Leu | AAA Lys | GCT Ala 630 | GAC Asp | TTT Phe | 1983 |
| CCA Pro | GAC Asp | AAT Asn | ATT Ile 635 | GTG Val | ATC Ile | GCC Ala | AGC Ser | ATC Ile 640 | ATG Met | TGT Cys | AGT Ser | TAC Tyr | AAC Asn 645 | AAA Lys | AAT Asn | 2031 |
| GAC Asp | TGG Trp | ATG Met 650 | GAA Glu | CTC Leu | TCC Ser | AGA Arg | AAG Lys 655 | GCT Ala | GAG Glu | GCC Ala | TCT Ser | GGA Gly 660 | GCA Ala | GAT Asp | GCC Ala | 2079 |
| TTG Leu | GAG Glu 665 | TTA Leu | AAT Asn | CTG Leu | TCA Ser | TGT Cys 670 | CCA Pro | CAC His | GGC Gly | ATG Met | GGA Gly 675 | GAA Glu | AGA Arg | GGA Gly | ATG Met 680 | 2127 |
| GGC Gly | CTG Leu | GCT Ala | TGT Cys | GGG Gly 685 | CAG Gln | GAT Asp | CCA Pro | GAG Glu | CTG Leu 690 | GTG Val | CGG Arg | AAC Asn | ATC Ile | TGT Cys 695 | CGC Arg | 2175 |
| TGG Trp | GTT Val | AGG Arg | CAA Gln 700 | GCT Ala | GTT Val | CAG Gln | ATT Ile | CCC Pro 705 | TTT Phe | TTT Phe | GCC Ala | AAG Lys | TTG Leu 710 | ACC Thr | CCA Pro | 2223 |
| AAC Asn | GTC Val | ACT Thr 715 | GAT Asp | ATA Ile | GTA Val | AGC Ser | ATC Ile 720 | GCC Ala | AGA Arg | GCG Ala | GCC Ala | AAG Lys 725 | GAA Glu | GGT Gly | GGC Gly | 2271 |
| GCA Ala | GAT Asp | GGT Gly 730 | GTT Val | ACA Thr | GCC Ala | ACC Thr 735 | AAC Asn | ACG Thr | GTC Val | TCA Ser | GGT Gly 740 | CTC Leu | ATG Met | GGA Gly | TTA Leu | 2319 |
| AAA Lys | GCC Ala | GAT Asp | GGC Gly | ACG Thr | CCC Pro | TGG Trp | CCA Pro | GCG Ala | GTG Val | GGT Gly | GCT Ala | GGC Gly | AAG Lys | CGG Arg | ACT Thr | 2367 |

-continued

```
Lys Ala Asp Gly Thr Pro Trp Pro Ala Val Gly Ala Gly Lys Arg Thr
745                 750                 755                 760

ACA TAC GGA GGA GTG TCT GGC ACG GCC ATC AGA CCA ATT GCT TTG AGA    2415
Thr Tyr Gly Gly Val Ser Gly Thr Ala Ile Arg Pro Ile Ala Leu Arg
                765                 770                 775

GCT GTG ACC ACC ATT GCT CGT GCT TTG CCT GGA TTT CCC ATT TTG GCT    2463
Ala Val Thr Thr Ile Ala Arg Ala Leu Pro Gly Phe Pro Ile Leu Ala
            780                 785                 790

ACT GGT GGA ATT GAC TCA GCT GAA AGT GGA CTT CAG TTT CTC CAC AGT    2511
Thr Gly Gly Ile Asp Ser Ala Glu Ser Gly Leu Gln Phe Leu His Ser
        795                 800                 805

GGT GCT TCG GTC CTC CAG GTA TGC AGT GCT GTT CAG AAT CAG GAT TTC    2559
Gly Ala Ser Val Leu Gln Val Cys Ser Ala Val Gln Asn Gln Asp Phe
    810                 815                 820

ACT GTC ATC CAA GAC TAT TGC ACT GGC CTC AAA GCC TTG CTT TAT CTG    2607
Thr Val Ile Gln Asp Tyr Cys Thr Gly Leu Lys Ala Leu Leu Tyr Leu
825                 830                 835                 840

AAA AGC ATT GAA GAA CTA CAA GGC TGG GAT GGG CAG AGT CCA GGT ACC    2655
Lys Ser Ile Glu Glu Leu Gln Gly Trp Asp Gly Gln Ser Pro Gly Thr
                845                 850                 855

GAG AGT CAC CAG AAG GGG AAA CCA GTT CCT CGT ATT GCT GAA CTC ATG    2703
Glu Ser His Gln Lys Gly Lys Pro Val Pro Arg Ile Ala Glu Leu Met
            860                 865                 870

GGA AAG AAA CTG CCA AAT TTT GGA CCT TAT CTG GAG CAA CGC AAG AAA    2751
Gly Lys Lys Leu Pro Asn Phe Gly Pro Tyr Leu Glu Gln Arg Lys Lys
        875                 880                 885

ATC ATA GCA GAG GAA AAG ATG AGA CTG AAA GAA CAA AAT GCA GCT TTT    2799
Ile Ile Ala Glu Glu Lys Met Arg Leu Lys Glu Gln Asn Ala Ala Phe
    890                 895                 900

CCA CCA CTT GAG AGA AAA CCT TTT ATT CCC AAA AAG CCT ATT CCT GCT    2847
Pro Pro Leu Glu Arg Lys Pro Phe Ile Pro Lys Lys Pro Ile Pro Ala
905                 910                 915                 920

ATT AAG GAT GTA ATT GGA AAA GCA CTG CAG TAC CTT GGA ACG TTT GGT    2895
Ile Lys Asp Val Ile Gly Lys Ala Leu Gln Tyr Leu Gly Thr Phe Gly
                925                 930                 935

GAA CTG AGC AAC ATA GAG CAA GTT GTG GCT GTG ATC GAT GAA GAA ATG    2943
Glu Leu Ser Asn Ile Glu Gln Val Val Ala Val Ile Asp Glu Glu Met
            940                 945                 950

TGT ATC AAC TGT GGC AAA TGC TAC ATG ACC TGT AAT GAC TCT GGC TAC    2991
Cys Ile Asn Cys Gly Lys Cys Tyr Met Thr Cys Asn Asp Ser Gly Tyr
        955                 960                 965

CAG GCT ATC CAG TTT GAT CCC GAA ACC CAC CTG CCC ACC GTT ACT GAC    3039
Gln Ala Ile Gln Phe Asp Pro Glu Thr His Leu Pro Thr Val Thr Asp
    970                 975                 980

ACT TGC ACA GGC TGT ACC CTG TGT CTC TCC GTC TGC CCT ATT ATC GAC    3087
Thr Cys Thr Gly Cys Thr Leu Cys Leu Ser Val Cys Pro Ile Ile Asp
985                 990                 995                 1000

TGC ATC AGA ATG GTT TCC AGG ACA ACA CCT TAC GAA CCA AAG AGA GGC    3135
Cys Ile Arg Met Val Ser Arg Thr Thr Pro Tyr Glu Pro Lys Arg Gly
                1005                1010                1015

TTG CCC TTG GCT GTG AAT CCG GTG TGC TGAGGTGATT CGTGGAACAG          3182
Leu Pro Leu Ala Val Asn Pro Val Cys
            1020                1025

TTGCTGTGAA CTTTGAGGTC ACCCCCATAT GCTGTCTTTT TAATTGTGGT TATTATACTC  3242

AGCTCTTTCT CAATGAAAAC AAATATAATA TTTCTAGATA AAAGTTCTAA ATACATGTCT  3302

AAATTTTAAA AAACATCTAC TGCCAGAGCC CGTTCAATTA ATGGTCATAA AATAGAATCC  3362

TGCTTTTCTG AGGCTAGTTG TTCAATAACT GCTGCAGTTA ATTGGATGTT CTCCATCAGT  3422

TATCCATTAT GAAAAATATT AACTTTTTTG GTGGCAATTT CCAAATTGCC CTATGCTGTG  3482
```

-continued

```
CTCTGTCTTT   GATTTCTAAT   TGTAAGTGAA   GTTAAGCATT   TTAGAACAAA   GTATAATTTA      3542
ACTTTCAAGC   AAATGTTTCC   AAGGAAACAT   TTTATAATTA   AAAATTACAA   TTTAATTTTA      3602
ACACTGTTCC   TAAGCAAATG   TAATTAGCTC   CATAAAGCTC   AAATGAAGTC   AAATAATTAT      3662
TTACTGTGGC   AGGAAAAGAA   AGCCAATGAG   GGTTTGCAAA   ACTTCTCTAA   GGCCCTTTGG      3722
CTGAAATAAC   TTCTCTTTGG   TGCTACATAC   TGAAAGTGAC   TGTTAATCA    TCATTCATGT      3782
CACACCGTGC   TCCCTCGCCC   TCAGGCCTGA   GATGGGTCTC   CAGACTCCAC   CAGTGAATCA      3842
GCATGACACC   TTCTTTAACT   GTGTGAGCGA   CGTTCCTAAC   AAAGTAAGGT   GTGGGGATGA      3902
AGCTCTGGTT   AAAGCCACTC   TTTTGCTGTG   CTCCGATCTG   TTCTATCCGC   TTCTGAGAGC      3962
AACCTTCATG   ATTACAGCAA   TTAATGTTTG   CACAGAGCCC   AGATTATACA   GCAGTGGGTC      4022
ATTGTGCTTC   ATTATTCAAG   AATGAAGATA   AAGACAAATA   GAGGATTAGT   AAAATATATT      4082
AAATGTGCAA   TACCACTTAA   ATGACTCTTA   ATGTTTATAT   TGAATTCCA    AAGCGATTAA      4142
ATAAAAAGA    GCTATTTTTT   GTTATTGCCA   AACAATATTT   TTTGTATTTC   TCTATTTTCA      4202
TAATGAGCAA   ATAGCATCCT   ATAAATCTGT   TTATCTCTTC   TTTGTAGTGT   GTTTTCATAT      4262
AAATCCACAA   GTAGAAAATC   TTTTCATCTG   TGGCATATTT   CTATGACAAA   TGCAAGATCT      4322
AGAAAAATTA   AATGTTTGAT   TATGCCATTT   TGGAAATGCA   TATTTACCAC   CAAACCTATG      4382
TGACTGAATA   ATGTCAAATA   AAATTTTATG   AATCATTTTA   AAAAAAAAA    AAAAAGGGCG      4442
GCCGC                                                                           4447
```

( 2 ) INFORMATION FOR SEQ ID NO:4:

( i ) SEQUENCE CHARACTERISTICS:
        ( A ) LENGTH: 1025 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Pro  Val  Leu  Ser  Lys  Asp  Val  Ala  Asp  Ile  Glu  Ser  Ile  Leu
  1                   5                  10                  15

Ala  Leu  Asn  Pro  Arg  Thr  Gln  Ser  His  Ala  Ala  Leu  His  Ser  Thr  Leu
             20                  25                  30

Ala  Lys  Lys  Leu  Asp  Lys  Lys  His  Trp  Lys  Arg  Asn  Pro  Asp  Lys  Asn
        35                  40                  45

Cys  Phe  His  Cys  Glu  Lys  Leu  Glu  Asn  Asn  Phe  Gly  Asp  Ile  Lys  His
        50                  55                  60

Thr  Thr  Leu  Gly  Glu  Arg  Gly  Ala  Leu  Arg  Glu  Ala  Met  Arg  Cys  Leu
 65                  70                  75                  80

Lys  Cys  Ala  Asp  Ala  Pro  Cys  Gln  Lys  Ser  Cys  Pro  Thr  His  Leu  Asp
                  85                  90                  95

Ile  Lys  Ser  Phe  Ile  Thr  Ser  Ile  Ser  Asn  Lys  Asn  Tyr  Tyr  Gly  Ala
                 100                 105                 110

Ala  Lys  Met  Ile  Phe  Ser  Asp  Asn  Pro  Leu  Gly  Leu  Thr  Cys  Gly  Met
             115                 120                 125

Val  Cys  Pro  Thr  Ser  Asp  Leu  Cys  Val  Gly  Gly  Cys  Asn  Leu  Tyr  Ala
        130                 135                 140

Thr  Glu  Glu  Gly  Ser  Ile  Asn  Ile  Gly  Gly  Leu  Gln  Gln  Phe  Ala  Ser
145                 150                 155                 160

Glu  Val  Phe  Lys  Ala  Met  Asn  Ile  Pro  Gln  Ile  Arg  Asn  Pro  Cys  Leu
                 165                 170                 175
```

```
Pro  Ser  Gln  Glu  Lys  Met  Pro  Glu  Ala  Tyr  Ser  Ala  Lys  Ile  Ala  Leu
               180                 185                      190

Leu  Gly  Ala  Gly  Pro  Ala  Ser  Ile  Ser  Cys  Ala  Ser  Phe  Leu  Ala  Arg
          195                      200                 205

Leu  Gly  Tyr  Ser  Asp  Ile  Thr  Ile  Phe  Glu  Lys  Glu  Tyr  Val  Gly
     210                      215                 220

Gly  Leu  Ser  Thr  Ser  Glu  Ile  Pro  Gln  Phe  Arg  Leu  Pro  Tyr  Asp  Val
225                      230                 235                           240

Val  Asn  Phe  Glu  Ile  Glu  Leu  Met  Lys  Asp  Leu  Gly  Val  Lys  Ile  Ile
               245                 250                      255

Cys  Gly  Lys  Ser  Leu  Ser  Glu  Asn  Glu  Ile  Thr  Leu  Asn  Thr  Leu  Lys
               260                 265                      270

Glu  Glu  Gly  Tyr  Lys  Ala  Ala  Phe  Ile  Gly  Ile  Gly  Leu  Pro  Glu  Pro
          275                      280                 285

Lys  Thr  Asp  Asp  Ile  Phe  Gln  Gly  Leu  Thr  Gln  Asp  Gln  Gly  Phe  Tyr
     290                      295                 300

Thr  Ser  Lys  Asp  Phe  Leu  Pro  Leu  Val  Ala  Lys  Ser  Ser  Lys  Ala  Gly
305                      310                 315                           320

Met  Cys  Ala  Cys  His  Ser  Pro  Leu  Pro  Ser  Ile  Arg  Gly  Ala  Val  Ile
               325                 330                      335

Val  Leu  Gly  Ala  Gly  Asp  Thr  Ala  Phe  Asp  Cys  Ala  Thr  Ser  Ala  Leu
          340                      345                 350

Arg  Cys  Gly  Ala  Arg  Arg  Val  Phe  Leu  Val  Phe  Arg  Lys  Gly  Phe  Val
     355                      360                 365

Asn  Ile  Arg  Ala  Val  Pro  Glu  Glu  Val  Glu  Leu  Ala  Lys  Glu  Glu  Lys
     370                      375                 380

Cys  Glu  Phe  Leu  Pro  Phe  Leu  Ser  Pro  Arg  Lys  Val  Ile  Val  Lys  Gly
385                      390                 395                           400

Gly  Arg  Ile  Val  Ala  Val  Gln  Phe  Val  Arg  Thr  Glu  Gln  Asp  Glu  Thr
               405                      410                 415

Gly  Lys  Trp  Asn  Glu  Asp  Glu  Asp  Gln  Ile  Val  His  Leu  Lys  Ala  Asp
               420                 425                      430

Val  Val  Ile  Ser  Ala  Phe  Gly  Ser  Val  Leu  Arg  Asp  Pro  Lys  Val  Lys
               435                      440                 445

Glu  Ala  Leu  Ser  Pro  Ile  Lys  Phe  Asn  Arg  Trp  Asp  Leu  Pro  Glu  Val
450                      455                 460

Asp  Pro  Glu  Thr  Met  Gln  Thr  Ser  Glu  Pro  Trp  Val  Phe  Ala  Gly  Gly
465                      470                 475                           480

Asp  Ile  Val  Gly  Met  Ala  Asn  Thr  Thr  Val  Glu  Ser  Val  Asn  Asp  Gly
                    485                 490                      495

Lys  Gln  Ala  Ser  Trp  Tyr  Ile  His  Lys  Tyr  Ile  Gln  Ala  Gln  Tyr  Gly
               500                 505                      510

Ala  Ser  Val  Ser  Ala  Lys  Pro  Glu  Leu  Pro  Leu  Phe  Tyr  Thr  Pro  Val
          515                      520                 525

Asp  Leu  Val  Asp  Ile  Ser  Val  Glu  Met  Ala  Gly  Leu  Lys  Phe  Ile  Asn
     530                      535                 540

Pro  Phe  Gly  Leu  Ala  Ser  Ala  Ala  Pro  Thr  Thr  Ser  Ser  Ser  Met  Ile
545                      550                 555                           560

Arg  Arg  Ala  Phe  Glu  Ala  Gly  Trp  Gly  Phe  Ala  Leu  Thr  Lys  Thr  Phe
               565                      570                 575

Ser  Leu  Asp  Lys  Asp  Ile  Val  Thr  Asn  Val  Ser  Pro  Arg  Ile  Val  Arg
               580                      585                 590

Gly  Thr  Thr  Ser  Gly  Pro  Met  Tyr  Gly  Pro  Gly  Gln  Ser  Ser  Phe  Leu
          595                      600                 605
```

```
Asn Ile Glu Leu Ile Ser Glu Lys Thr Ala Ala Tyr Trp Cys Gln Ser
    610             615                 620
Val Thr Glu Leu Lys Ala Asp Phe Pro Asp Asn Ile Val Ile Ala Ser
625             630                 635                 640
Ile Met Cys Ser Tyr Asn Lys Asn Asp Trp Met Glu Leu Ser Arg Lys
                645                 650                 655
Ala Glu Ala Ser Gly Ala Asp Ala Leu Glu Leu Asn Leu Ser Cys Pro
            660                 665                 670
His Gly Met Gly Glu Arg Gly Met Gly Leu Ala Cys Gly Gln Asp Pro
        675                 680                 685
Glu Leu Val Arg Asn Ile Cys Arg Trp Val Arg Gln Ala Val Gln Ile
    690                 695                 700
Pro Phe Phe Ala Lys Leu Thr Pro Asn Val Thr Asp Ile Val Ser Ile
705                 710                 715                 720
Ala Arg Ala Ala Lys Glu Gly Gly Ala Asp Gly Val Thr Ala Thr Asn
                725                 730                 735
Thr Val Ser Gly Leu Met Gly Leu Lys Ala Asp Gly Thr Pro Trp Pro
            740                 745                 750
Ala Val Gly Ala Gly Lys Arg Thr Thr Tyr Gly Gly Val Ser Gly Thr
        755                 760                 765
Ala Ile Arg Pro Ile Ala Leu Arg Ala Val Thr Thr Ile Ala Arg Ala
    770                 775                 780
Leu Pro Gly Phe Pro Ile Leu Ala Thr Gly Gly Ile Asp Ser Ala Glu
785                 790                 795                 800
Ser Gly Leu Gln Phe Leu His Ser Gly Ala Ser Val Leu Gln Val Cys
                805                 810                 815
Ser Ala Val Gln Asn Gln Asp Phe Thr Val Ile Gln Asp Tyr Cys Thr
            820                 825                 830
Gly Leu Lys Ala Leu Leu Tyr Leu Lys Ser Ile Glu Glu Leu Gln Gly
        835                 840                 845
Trp Asp Gly Gln Ser Pro Gly Thr Glu Ser His Gln Lys Gly Lys Pro
    850                 855                 860
Val Pro Arg Ile Ala Glu Leu Met Gly Lys Lys Leu Pro Asn Phe Gly
865                 870                 875                 880
Pro Tyr Leu Glu Gln Arg Lys Lys Ile Ile Ala Glu Glu Lys Met Arg
                885                 890                 895
Leu Lys Glu Gln Asn Ala Ala Phe Pro Pro Leu Glu Arg Lys Pro Phe
            900                 905                 910
Ile Pro Lys Lys Pro Ile Pro Ala Ile Lys Asp Val Ile Gly Lys Ala
        915                 920                 925
Leu Gln Tyr Leu Gly Thr Phe Gly Glu Leu Ser Asn Ile Glu Gln Val
    930                 935                 940
Val Ala Val Ile Asp Glu Glu Met Cys Ile Asn Cys Gly Lys Cys Tyr
945                 950                 955                 960
Met Thr Cys Asn Asp Ser Gly Tyr Gln Ala Ile Gln Phe Asp Pro Glu
                965                 970                 975
Thr His Leu Pro Thr Val Thr Asp Thr Cys Thr Gly Cys Thr Leu Cys
            980                 985                 990
Leu Ser Val Cys Pro Ile Ile Asp Cys Ile Arg Met Val Ser Arg Thr
        995                 1000                1005
Thr Pro Tyr Glu Pro Lys Arg Gly Leu Pro Leu Ala Val Asn Pro Val
    1010                1015                1020
Cys
```

1025

(2) INFORMATION FOR SEQ ID NO:5:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:5:

GCAAGGAGGG TTTGTCACTG                     20

(2) INFORMATION FOR SEQ ID NO:6:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:6:

CCGATTCCAC TGTAGTGTTA GCC                  23

(2) INFORMATION FOR SEQ ID NO:7:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:7:

TAACACTACA GTGGAATCGG                     20

(2) INFORMATION FOR SEQ ID NO:8:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:8:

AAATCCAGGC AGAGCACGAG                     20

(2) INFORMATION FOR SEQ ID NO:9:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:9:

TGCTCGTGCT CTGCCTGGAT TTCC                  24

(2) INFORMATION FOR SEQ ID NO:10:

```
( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:10:

ATTGAATGGT  CATTGACATG  AGAC                                                    2 4

( 2 ) INFORMATION FOR SEQ ID NO:11:

( i ) SEQUENCE CHARACTERISTICS:
            ( A ) LENGTH: 12 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:11:

Cys   Xaa   Xaa   Cys   Xaa   Xaa   Cys   Xaa   Xaa   Cys   Xaa
     1                       5                               1 0

( 2 ) INFORMATION FOR SEQ ID NO:12:

( i ) SEQUENCE CHARACTERISTICS:
            ( A ) LENGTH: 12 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:12:

Cys   Xaa   Xaa   Cys   Xaa   Xaa   Cys   Xaa   Xaa   Xaa   Cys   Pro
     1                       5                               1 0

( 2 ) INFORMATION FOR SEQ ID NO:13:

( i ) SEQUENCE CHARACTERISTICS:
            ( A ) LENGTH: 17 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:13:

Val   Xaa   Val   Xaa   Gly   Xaa   Gly   Xaa   Xaa   Gly   Xaa   Xaa   Xaa   Ala   Xaa   Xaa
     1                       5                               1 0                          1 5

Ala
```